United States Patent
Stevens et al.

(10) Patent No.: US 11,562,257 B2
(45) Date of Patent: Jan. 24, 2023

(54) IDENTIFYING KNOWLEDGE GAPS UTILIZING COGNITIVE NETWORK META-ANALYSIS

(71) Applicant: International Business Machines Corporation, Armonk, NY (US)

(72) Inventors: Richard J. Stevens, Monkton, VT (US); Fernando Jose Suarez Saiz, Armonk, NY (US); Eric W. Will, Rochester, MN (US); Adam Clark, Mantorville, MN (US)

(73) Assignee: MERATIVE US L.P., Ann Arbor, MI (US)

(*) Notice: Subject to any disclaimer, the term of this patent is extended or adjusted under 35 U.S.C. 154(b) by 938 days.

(21) Appl. No.: 16/202,889

(22) Filed: Nov. 28, 2018

(65) Prior Publication Data

US 2020/0167664 A1    May 28, 2020

(51) Int. Cl.
*G06N 5/02* (2006.01)
*G16H 50/70* (2018.01)
*G16H 20/00* (2018.01)
*G16B 40/00* (2019.01)
*G16B 50/00* (2019.01)

(52) U.S. Cl.
CPC .............. *G06N 5/02* (2013.01); *G16B 40/00* (2019.02); *G16B 50/00* (2019.02); *G16H 20/00* (2018.01); *G16H 50/70* (2018.01)

(58) Field of Classification Search
None
See application file for complete search history.

(56) References Cited

U.S. PATENT DOCUMENTS

| | | | |
|---|---|---|---|
| 8,793,145 B2 | 7/2014 | Kahn et al. | |
| 9,003,319 B2 | 4/2015 | Linthicum et al. | |
| 9,477,781 B2 | 10/2016 | Shyr et al. | |
| 9,639,667 B2 | 5/2017 | Rosano et al. | |
| 9,734,289 B2 | 8/2017 | Pecora | |
| 9,996,662 B1 | 6/2018 | Florissi et al. | |
| 10,007,879 B2 | 6/2018 | Kakrania et al. | |
| 2008/0294582 A1 | 11/2008 | de Kleer | |
| 2014/0200824 A1 | 7/2014 | Pancoska | |
| 2014/0278517 A1 | 9/2014 | Patel et al. | |
| 2015/0242569 A1 | 8/2015 | Antony et al. | |
| 2017/0068789 A1 | 3/2017 | Dalton et al. | |
| 2018/0218127 A1 | 8/2018 | Salazar et al. | |

OTHER PUBLICATIONS

Tramacere, Irene, et al. "Immunomodulators and immunosuppressants for relapsing-remitting multiple sclerosis: a network meta-analysis." Cochrane Database of Systematic Reviews 9 (2015).*
Krahn et al.; "Visualizing Inconsistency In Network Meta-Analysis By Independent Paths Decomposition", BMC Medical Research Method 2014, 14:131, Dec. 16, 2014, pp. 1-12.
Papakonstantinou et al.; "Estimating The Contribution Of studies In Network Meta-Analysis: Paths, Flows, And Streams", F1000 Research, vol. 7:610, May 18, 2018, pp. 1-17Chaimani et al.; "Graph Tools For Network Meta-Analysis In STATA", PLoS ONE, vol. 18, Issue 10, Octobers, 2013, e76654, pp. 1-12.
Salanti et al.; "Planning A Future Randomized Clinical Trial Based On A Network Of Relevant Past Trials", TRIALS 19:365, Jul. 11, 2018, pp. 1-7.
Chaimani A, Higgins JPT, Mavridis D, Spyridonos P, Salanti G (2013) Graphical Tools for Network Meta-Analysis in STATA. PLoS One 8(10): e76654. doi:10.1371/journal.pone.0076654.

* cited by examiner

*Primary Examiner* — G Steven Vanni
(74) *Attorney, Agent, or Firm* — Patterson + Sheridan, LLP

(57) ABSTRACT

Techniques for identifying missing evidence are provided. A plurality of documents, each comprising digitally encoded natural language text data, is received. The plurality of documents is processed to determine a plurality of pair-wise comparisons between a plurality of therapies, where each of the plurality of pair-wise comparisons indicate a relative efficacy of at least one therapy in the plurality of therapies, as compared to at least one other therapy in the plurality of therapies. A knowledge graph is generated based at least in part on aggregating the plurality of pair-wise comparisons, and the knowledge graph is analyzed to identify one or more knowledge gaps within the knowledge graph. Finally, at least an indication of the identified one or more knowledge gaps is output.

20 Claims, 12 Drawing Sheets

IDENTIFYING KNOWLEDGE GAPS UTILIZING COGNITIVE NETWORK META-ANALYSIS

BACKGROUND

The present disclosure relates to analyzing knowledge graphs, and more specifically, to cognitively interpreting knowledge graphs to identify gaps or missing evidence.

In a variety of domains, studies, experiments, and trials are performed to understand how potential options or selections interact and compare to each other. For example, in the medical field, studies and trials are performed to determine the efficacy of new and existing therapies, in order to determine the best practices for treating or curing illnesses or disorders. Frequently, the results of these studies, experiments, and trials are published for review by others. Currently, the published literature is reviewed manually by subject-matter experts (SMEs) to determine the state of the field, and provide guidance with respect to optimal therapies. However, these determinations are time-consuming, expensive, and inherently biased. Further, the published literature is expanding at an increasing and unprecedented rate. As the number of published documents increases, it has become impossible to aggregate and interpret them all. Thus, current guidelines and best practices are universally outdated, and potentially conflict with newly discovered therapies or interactions. Additionally, the tremendous amount of data (and rapid pace with which new publications are released) makes it impossible to identify gaps in the data, or places where supporting evidence is weak or missing.

SUMMARY

According to one embodiment of the present disclosure, a method is provided. The method includes receiving a plurality of documents, each comprising digitally encoded natural language text data. The method further includes processing the plurality of documents to determine a plurality of pair-wise comparisons between a plurality of therapies, wherein each of the plurality of pair-wise comparisons indicate a relative efficacy of at least one therapy in the plurality of therapies, as compared to at least one other therapy in the plurality of therapies. Additionally, the method includes generating a knowledge graph, by operation of one or more processors, based at least in part on aggregating the plurality of pair-wise comparisons. Finally, the method includes analyzing the knowledge graph to identify one or more knowledge gaps within the knowledge graph, and outputting at least an indication of the identified one or more knowledge gaps.

According to a second embodiment of the present disclosure, a computer program product is provided. The computer program product comprises a computer-readable storage medium having computer-readable program code embodied therewith, the computer-readable program code executable by one or more computer processors to perform an operation. The operation includes receiving a plurality of documents, each comprising digitally encoded natural language text data. The operation further includes processing the plurality of documents to determine a plurality of pair-wise comparisons between a plurality of therapies, wherein each of the plurality of pair-wise comparisons indicate a relative efficacy of at least one therapy in the plurality of therapies, as compared to at least one other therapy in the plurality of therapies. Additionally, the operation includes generating a knowledge graph based at least in part on aggregating the plurality of pair-wise comparisons. Finally, the operation includes analyzing the knowledge graph to identify one or more knowledge gaps within the knowledge graph, and outputting at least an indication of the identified one or more knowledge gaps.

According to a third embodiment of the present disclosure, a system is provided. The system includes one or more computer processors and a memory containing a program which when executed by the one or more computer processors performs an operation. The operation includes receiving a plurality of documents, each comprising digitally encoded natural language text data. The operation further includes processing the plurality of documents to determine a plurality of pair-wise comparisons between a plurality of therapies, wherein each of the plurality of pair-wise comparisons indicate a relative efficacy of at least one therapy in the plurality of therapies, as compared to at least one other therapy in the plurality of therapies. Additionally, the operation includes generating a knowledge graph based at least in part on aggregating the plurality of pair-wise comparisons. Finally, the operation includes analyzing the knowledge graph to identify one or more knowledge gaps within the knowledge graph, and outputting at least an indication of the identified one or more knowledge gaps.

DETAILED DESCRIPTION

Figure 1:
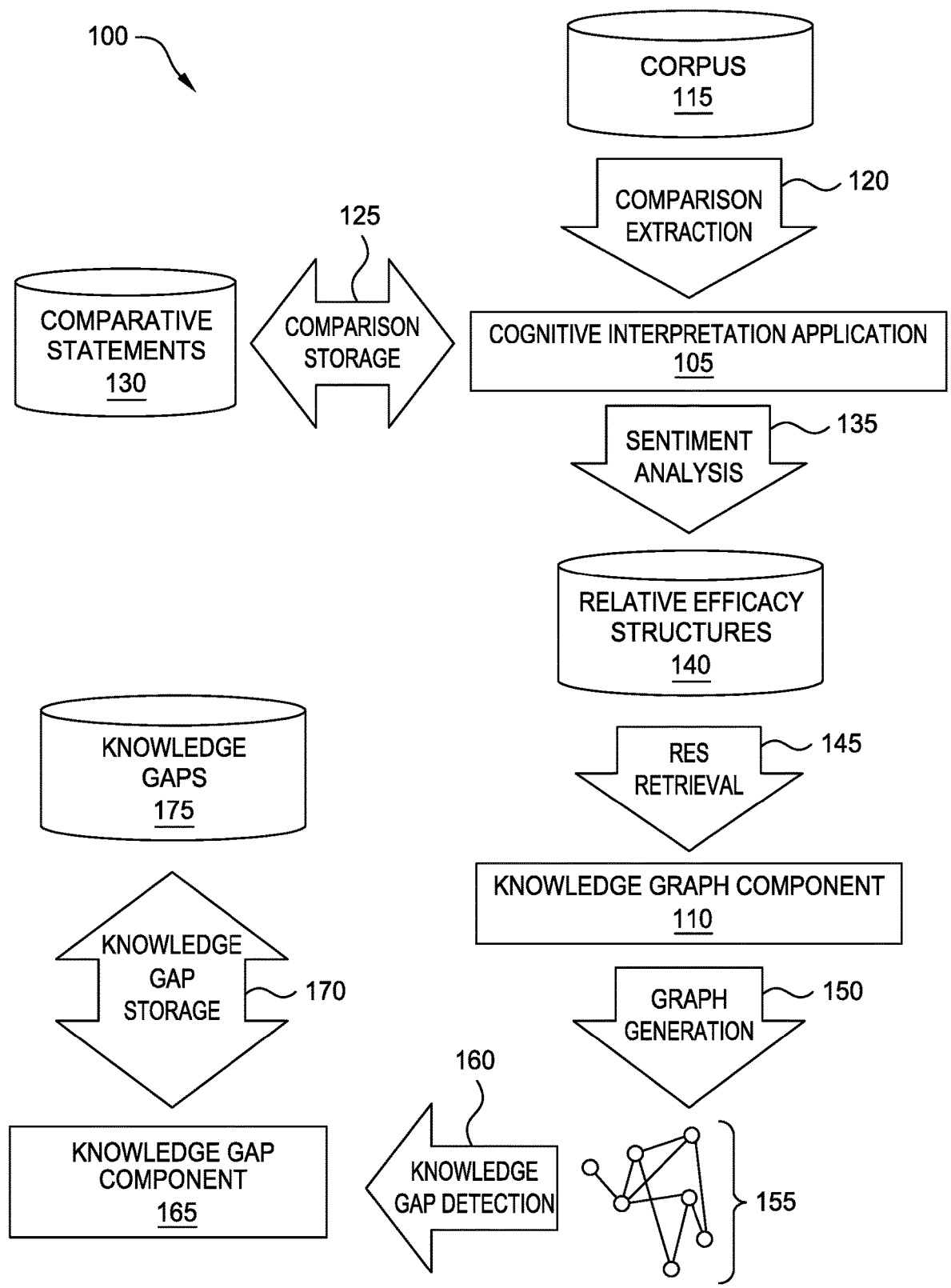
FIG. 1 illustrates a workflow for cognitively determining the relative efficacy of therapies, according to one embodiment disclosed herein.

In an embodiment of the present disclosure, a knowledge graph is analyzed to identify gaps or missing evidence. In one embodiment, these knowledge gaps indicate areas of the domain that may be valuable for additional study or research. In embodiments, the gaps can include places with weak evidence or connections, comparisons or trials that have not been conducted but that would help build on the existing corpus of knowledge, potential new therapies to study, and the like. In some embodiments, knowledge gaps in a graph are identified and scored based on a variety of factors, including the number of affected patients, the prognosis of the cohort, the number and efficacy of known therapies, the topology of the knowledge graph, and the like. In some embodiments, additional practical factors such as the availability of patients to participate in a study, the cost of a study, and the like are also considered. In an embodiment, before gaps or missing pieces in our knowledge can be identified, a knowledge graph must be constructed.

In some embodiments of the present disclosure, techniques for cognitive analysis, representation, and interpretation of published literature are provided. In one embodiment, a corpus of medical literature is parsed and analyzed to identify and extract comparative statements or opinions made by the authors of the paper. For example, in a conclusion or summary, the authors may indicate that a particular therapy showed improved results, as compared to one or more other therapies (or as compared to the known or popular literature and practices). These conclusions are provided in natural language text, and are rarely structured in a way that allows for easy ingestion of the information. Embodiments of the present disclosure are discussed with reference to medical literature. However, these examples are not limiting on the present disclosure, and one of skill in the art will recognize other domains and literature that the present embodiments can be applied to.

In one embodiment, these comparative statements are interpreted to determine a sentiment of the statement, and the relative efficacy of each therapy discussed. In some embodiments, a data structure, referred to herein as a relative efficacy structure or RES, is generated to capture the natural language comparative statement in a useful format. For example, in one embodiment, the RES has a number of dimensions, including the directionality of the comparison (e.g., which therapy is superior), the magnitude of the difference, the particular outcome the statement refers to (e.g., survival, progression-free survival, remission, etc.), qualifiers of the statement (e.g., limitations or specifications), and the like. In an embodiment, each RES is also associated with a weight, which is based on a variety of factors related to the underlying comparative statement and the nature of the article it is contained in.

In one embodiment, if a comparison is found in one direction (e.g., that treatment A is better than treatment B), a complementary RES is created in the opposite direction (e.g., indicating that treatment B is worse than treatment A). In this way, queries for information for a given treatment or therapy can identify all documents that involve the therapy, regardless of whether the document deemed the therapy to be superior or inferior.

In some embodiments, a knowledge graph can be generated based on the determined relationships extracted from one or more published document. For example, in one embodiment, each node in the knowledge graph corresponds to a particular therapy, and each edge corresponds to one or more RESs. In this way, the knowledge graph can be interrogated or searched to identify optimal treatment options for a given patient, based on a tremendous variety of medical literature. In such an embodiment, patient outcomes are improved, as the current state of the literature can be captured and ingested into the knowledge graph rapidly, reducing or eliminating the need for SME review. Further, in embodiments, the RESs provide additional insight and knowledge that is not accessible or present in existing solutions. Thus, embodiments of the present disclosure enable high-precision searching, and allow users to analyze the literature at a more granular level.

In some embodiments, users can search or query the knowledge graph based on therapies, cohorts, disorders, and the like, to return a subset of the graph that is relevant to the search. Further, in some embodiments, nodes and/or connections can be selected to retrieve a link to any documents or published literature that was analyzed to create the node or edge. In this way, users can readily access the relevant literature, if they wish to investigate further or obtain more information about why the topology of the graph is shaped as it is, as well as why particular connections exist.

Embodiments of the present disclosure can be applied to extract and interpret comparative statements made in any field. In one embodiment, medical literature (e.g., published studies, trials, experiments, and the like) is ingested. In some embodiments, the literature is analyzed to identify comparisons or statements about relative efficacy between therapy options. In an embodiment, a therapy is any treatment used to treat a disorder. As used herein, therapies can include drugs, medications, exercises, surgeries, use of equipment, prescribed activities, and the like. Further, in embodiments, therapies can include refraining from certain activities and withdrawing or reducing treatments. Additionally, in embodiments, a therapy may include multiple treatments or prescribed activities (e.g., multiple medications). As used herein, a medical disorder can include any illness or medical condition, including but not limited to mental or physical disease, sickness, disability, infection, symptoms, conditions, or statuses.

FIG. 1 illustrates a workflow 100 for cognitively determining the relative efficacy of therapies, according to one embodiment disclosed herein. In the illustrated embodiment, a Cognitive Interpretation Application 105 analyzes documents to extract Comparative Statements 130 and generate RESs 140, and a Knowledge Graph Component 110 analyzes these RESs 140 to generate a Knowledge Graph 150. In some embodiments, a Knowledge Graph 150 is generated to aid visualization or understanding of the literature (although it may not actually be displayed). In some embodiments, however, the knowledge graph is not created, and the RESs 140 are used for other purposes. That is, in some embodiments, the generated RESs are usable or searchable by other systems or components, and can be utilized to aid understanding and improve treatment selection, without the construction of a knowledge graph.

Further, in the illustrated embodiment, a Knowledge Gap Component 165 receives and analyzes the generated Knowledge Graph 155, in order to perform Knowledge Gap Detection 160. In embodiments, this comprises analyzing the topology of the graph, as well as the individual efficacies and relative efficacies of therapies in it, to identify areas that are potentially valuable for further study. As illustrated by the Knowledge Gap Storage 170, these identified gaps are stored in a data store reserved for Knowledge Gaps 175. Although illustrated as discrete and distinct storage units, in embodiments, one or more of the Corpus 115, Comparative Statements 130, RESs 140, and Knowledge Gaps 175 can be stored in a single data store.

In the illustrated workflow 100, the Cognitive Interpretation Application 105 analyzes a Corpus 115 of documents to perform Comparison Extraction 120. In an embodiment, the Corpus 115 includes documents which include at least some portion of natural language text, which may or may not have comparative statements by the author(s). In some embodiments, the Corpus 115 corresponds to a particular domain of interest to a user. For example, in one embodiment, a larger corpus or collection of documents is searched to identify a subset of the documents that relate to a particular disorder, therapy, or set of disorders or therapies. In such an embodiment, this subset of documents makes up the Corpus 115. In some embodiments, the workflow 100 is performed on multiple corpora (e.g., once for each therapy or disorder).

In an embodiment, the Comparison Extraction 120 comprises utilizing one or more natural language processing (NLP) techniques to identify comparative statements in the text included in the Corpus 115. For example, in one embodiment, the Cognitive Interpretation Application 105 searches for comparative language (such as "superior," "better," "worse," "improved," and the like). In some embodiments, the Cognitive Interpretation Application 105 analyzes predefined sections of the documents to identify these comparative statements (e.g., the abstract, conclusion, methods, discussion, etc.). That is, in an embodiment, a user or administrator can specify portions or sections in the documents that should be analyzed. In other embodiments, the Cognitive Interpretation Application 105 analyzes the full text of the document. In one embodiment, the Cognitive Interpretation Application 105 first searches the identified sections (as identified by their headings or by metadata tags), and only parses the rest of the document if the specified section(s) do not include any comparative statements (or if the specified section(s) cannot be found or do not exist in the document).

In some embodiments, the Comparison Extraction 120 also includes remedying unknown terms in the statement, such as through disambiguation and acronym resolution. For example, if the comparative statement includes an acronym, in one embodiment, the Cognitive Interpretation Application 105 can expand the acronym. Similarly, if the statement includes ambiguous or general language (such as, "all treatments studied herein", "with respect to the relevant cohort," or "generic chemotherapy drugs"), the Cognitive Interpretation Application 105 can determine a meaning for the terms. In some embodiments, the Cognitive Interpretation Application 105 first parses the selected document to identify the meaning of the term. That is, the Cognitive Interpretation Application 105 attempts to find meaning for the unknown term by analyzing the text of the document in which the comparative statement was found using NLP techniques. If no satisfactory disambiguation is found (e.g., the confidence level of any potential disambiguations is below a threshold), the Cognitive Interpretation Application 105 can access other literature (or one or more knowledge graphs) to disambiguate the term. In some embodiments, if the true meaning is not found within the corresponding document, the confidence or weight of the extracted comparison is reduced.

In some embodiments, Comparison Extraction 120 includes annotation of the extracted comparative statements. For example, in one embodiment, the Cognitive Interpretation Application 105 utilizes one or more NLP techniques to identify the therapy or therapies involved in the statement, the qualifier or comparative term utilized, and the like. In some embodiments, the Cognitive Interpretation Application 105 also determines the cohort(s) to which the statement (s) apply, as discussed in more detail below. Additionally, in some embodiments, the Cognitive Interpretation Application 105 determines characteristics of the comparative statements, such as where in the text it was located (e.g., which section it was found in), the publication date of the document, whether the document has been peer-reviewed, an identity of the publisher or entity that provided the document, and the like.

In the illustrated embodiment, the Cognitive Interpretation Application 105 stores the extracted comparisons (e.g., the natural language text) in a data store for Comparative Statements 130. In some embodiments, these stored Comparative Statements 130 are annotated to identify the relevant therapies, qualifiers, and the like. In some embodiments, the Comparative Statements 130 also indicate the disorder that is relevant to the comparison. In other embodiments, the disorder is described by the cohort and/or cohort qualifiers. In embodiments, the Comparative Statements 130 can be stored locally by the Cognitive Interpretation Application 105, or in one or more remote storage locations (such as in the cloud). As illustrated, the Cognitive Interpretation Application 105 then performs Sentiment Analysis 135 on the extracted Comparative Statements 130, to generate a set of RESs 140. In an embodiment, this Sentiment Analysis 135 includes classifying each statement as positive, negative, or neutral with respect to each of the implicated therapies. In some embodiments, the Cognitive Interpretation Application 105 also determines a degree of the sentiment (based on, for example, the strength of the language or term used). Further, in some embodiments, the RESs 140 include an indication as to which outcome or outcome type the comparison relates to (e.g., overall survival, progression-free survival, etc.).

In some embodiments, the RESs 140 include an indication as to the therapies involved, the relevant cohort, and the like. In one embodiment, each RES 140 corresponds to a particular Comparative Statement 130. In one embodiment, each RES 140 is weighted based on a variety of factors. For example, in an embodiment, the weighting factors include how recently the corresponding document was published, whether the document has been peer-reviewed, the identity of the publisher or provider for the document, the number of patients evaluated in the clinical study, and the like. In one embodiment, publishers are associated with predefined weights or strengths, based on their prestige or trustworthiness. In some embodiments, the Cognitive Interpretation Application 105 weights each RES 140 based on a confidence level as well. In one embodiment, this confidence level is based in part on a confidence value returned by the NLP models. Further, in an embodiment, the confidence is adjusted based on where in the document the corresponding Comparative Statement 130 was found. For example, a comparison found in the abstract or conclusion can be given a higher weight, while a comparison found elsewhere in the document can be given a lower weight.

In the illustrated embodiment, the Knowledge Graph Component 110 retrieves these RESs 140 from the data store, and performs Graph Generation 150 to generate a Knowledge Graph 155. In an embodiment, each node in the Knowledge Graph 150 is a therapy (or combination of therapies), and each edge is based on the determined relationships and relative efficacies (e.g., the RESs 140). In one embodiment, the Knowledge Graph Component 110 adds an edge or connection for each determined RESs 140 (e.g., for each comparative statement found). In some embodiments, the Knowledge Graph Component 110 aggregates the comparisons. For example, in an embodiment, for each outcome type and cohort combination, the Knowledge Graph Component 110 can aggregate the corresponding RESs 140, in order to determine an overall relative efficacy for the therapies, with respect to the cohort and outcome. In some embodiments, this aggregation is based in part on the weights of each comparison, as discussed above.

As illustrated, the Knowledge Gap Component 165 can retrieve this Knowledge Graph 155 and analyze it to identify Knowledge Gaps 175, as discussed in more detail below. In embodiments, these gaps or missing evidence can include identifying therapies that have not been studied or are poorly studied with respect to a particular cohort. Further, in an embodiment, the gaps include identifying studies or trials that have been conducted, but further research would be valuable in clearing up inconsistencies or expanding the knowledge graph. In some embodiments, a user or administrator can indicate one or more cohorts and/or disorders that are of interest, and the Knowledge Gap Detection 160 can be limited to the identified cohorts and/or disorders. In an embodiment, the Knowledge Gap Component 165 identifies the gaps, and ranks them based on a variety of factors, as discussed below in more detail.

In one embodiment, the user or administrator can define weights for each cohort and/or disorder, such that the overall scoring or ranking of the potentially valuable areas is sorted based in part on the cohort and/or disorder it applies to. Further, in some embodiments, the user can define weights or preferences for particular types of gaps. For example, in one embodiment, the user may be particularly interested in studying areas or comparisons that have not been studied at all, or may prefer to conduct a trial to attempt to confirm or contradict previously-conducted studies. Similarly, a user may be particularly interested in finding new therapies that have not been tested with a particular cohort. Embodiments of the present disclosure enable users to control the weights and configurations of a variety of factors to tailor the resulting ranking, as discussed below in more detail.

Figure 2:
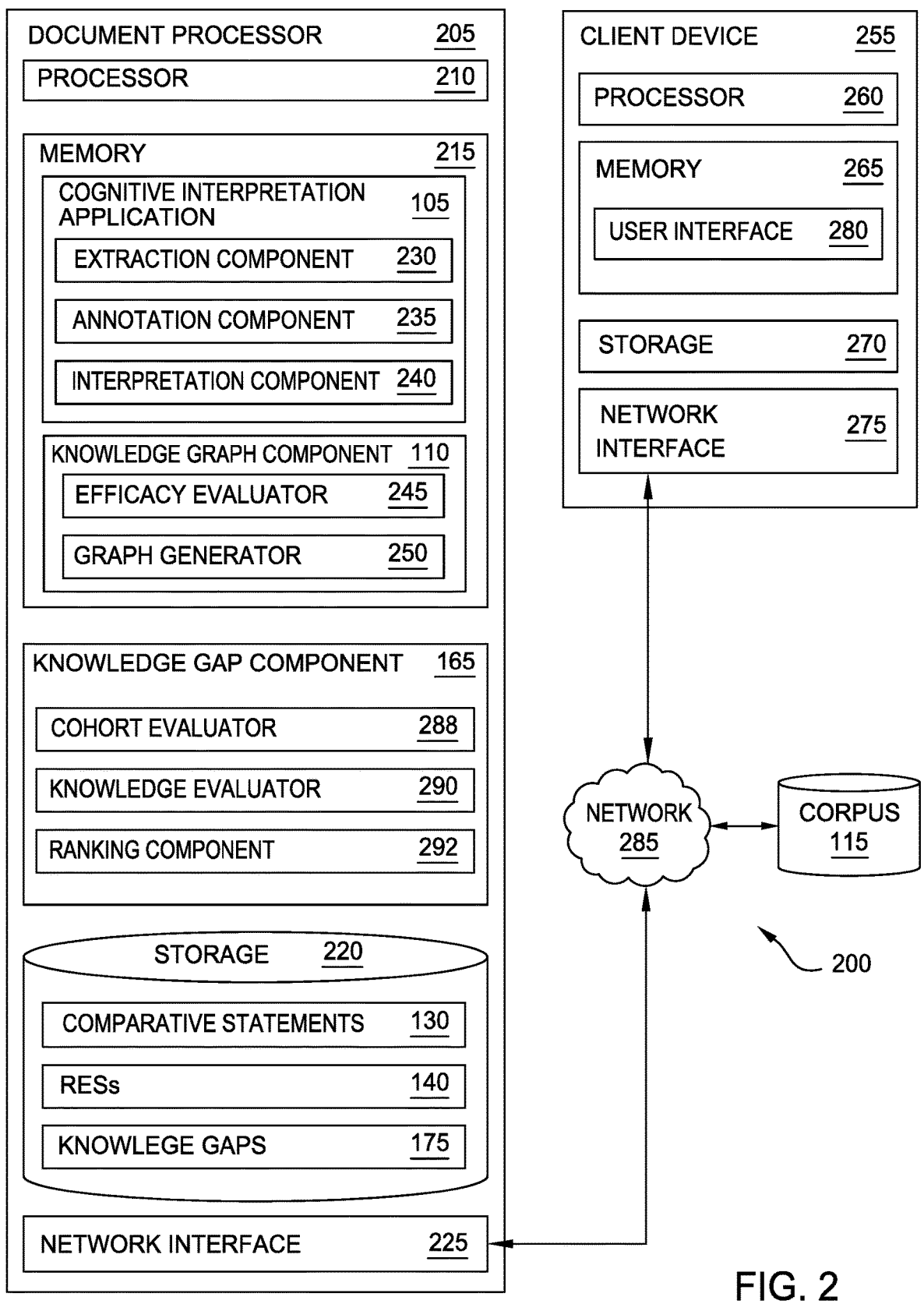
FIG. 2 is a block diagram of a system configured to cognitively determine the relative efficacy of therapies, according to one embodiment disclosed herein.

FIG. 2 is a block diagram of a system 200 configured to cognitively determine the relative efficacy of therapies, according to one embodiment disclosed herein. In the illustrated embodiment, the system 200 includes a Document Processor 205, a Client Device 255, and a Corpus 115. Although illustrated as discrete components, in embodiments, the Document Processor 205, Client Device 255, and Corpus 115 may operate or reside on a single device, or may be distributed across any number of devices. As illustrated, the Document Processor 205, Client Device 255, and Corpus 115 are communicatively linked through a Network 285. In one embodiment, the Network 285 is the Internet. Additionally, though a single Corpus 115 is illustrated, in embodiments, any number of corpora may be analyzed by the Document Processor 205.

As illustrated, the Document Processor 205 includes a Processor 210, a Memory 215, and Storage 220. In the illustrated embodiment, Processor 210 retrieves and executes programming instructions stored in Memory 215 as well as stores and retrieves application data residing in Storage 220. Processor 210 is representative of a single CPU, multiple CPUs, a single CPU having multiple processing cores, and the like. Memory 215 is generally included to be representative of a random access memory. Storage 220 may be a disk drive or flash-based storage device, and may include fixed and/or removable storage devices, such as fixed disk drives, removable memory cards, or optical storage, network attached storage (NAS), or storage area-network (SAN). Via the Network Interface 225, the Document Processor 205 can be communicatively coupled with corpuses of documents (such as Corpus 115), Client Devices 255, and the like.

In the illustrated embodiment, the Storage 220 of the Document Processor 205 includes a set of Comparative Statements 130, RESs 140, and Knowledge Gaps 175. In some embodiments, as discussed above, the Comparative Statements 130, RESs 140, and/or Knowledge Gaps 175 may be stored in one or more remote storage locations, such as in the cloud. As discussed above, in an embodiment, the Comparative Statements 130 are annotated natural language text extracts from documents in the Corpus 115. In one embodiment, each Comparative Statement 130 includes a comparison or opinion of the author of the corresponding document. In some embodiments, the annotations indicate the qualifier or comparator used by the author, the therapies implicated by the statement, the cohort or cohort qualifiers that limit the applicability of the comparison, and the like. Further, in some embodiments, the Comparative Statements 130 include publication characteristics of the statements, such as the location in their corresponding documents where they were found, the date of the publication, the entity that published it, and the like. Additionally, in one embodiment, the Comparative Statements 130 include an indication as to the confidence value that the NLP model(s) generated when parsing the statements.

As discussed above, in one embodiment, each RES 140 is a data structure representing a particular Comparative Statement 130. In some embodiments, each RES 140 indicates the therapies involved, the directionality or sentiment of the comparison, the cohort implicated, and the like. Further, in an embodiment, each RES 140 includes a weight, which can be based on a variety of factors including the publication characteristics of the underlying Comparative Statement 130, the confidence of the NLP model(s), and the like. In some embodiments, the RESs 140 are configured to be searchable, such that other systems or components (such as the Knowledge Graph Component 110) can readily access the information, and obtain an up-to-date and comprehensive understanding of the current state of the literature.

As discussed above, in an embodiment, each Knowledge Gap 175 corresponds to an area of the literature that is lacking evidence (or has sparse support). In some embodiments, at least some of the Knowledge Gaps 175 indicate a particular therapy or combination of therapies that should be studied in more detail. Similarly, in one embodiment, at least some of the Knowledge Gaps 175 indicate a particular cohort or set of patients that should be studied. In one embodiment, a Knowledge Gap 175 can include an indication that two or more therapies have not been directly compared (e.g., in a clinical trial), and that performing such a study has potential to improve the medical field. Similarly, in an embodiment, a Knowledge Gap 175 can indicate that two or more therapies have been compared previously, but that the supporting evidence is weak or conflicting, and thus that additional research may aid our collective understanding. Further, in one embodiment, a Knowledge Gap 175 may indicate that a particular cohort does not have any known treatments or therapies that are sufficiently effective, and thus that further study should be performed. In some embodiments, the Knowledge Gap 175 also indicates one or more therapies that have potential to be effective for the cohort.

In the illustrated embodiment, the Memory 215 of the Document Processor 205 includes a Cognitive Interpretation Application 105, a Knowledge Graph Component 110, and a Knowledge Gap Component 110. The Cognitive Interpretation Application 105 includes an Extraction Component 230, an Annotation Component 235, and an Interpretation Component 240. Although depicted as discrete components for illustration, in embodiments, the operations and functionality of the Extraction Component 230, Annotation Component 235, and Interpretation Component 240 can be combined or divided across any number of components. Further, although depicted as software components residing in Memory 215, in embodiments, the operations and functionality of the Extraction Component 230, Annotation Component 235, and Interpretation Component 240 can be implemented using hardware, software, or a combination of hardware and software.

In an embodiment, the Extraction Component 230 identifies and extracts statements that include comparisons between therapies or treatment options from documents in the Corpus 115, as discussed above. In some embodiments, the Extraction Component 230 utilizes one or more NLP techniques or models to identify the relevant text. Further, in an embodiment, the Annotation Component 235 annotates the extracted statements. In one embodiment, the Annotation Component 235 utilizes predefined rules, and/or additional NLP models and/or techniques to annotate the statements. These annotated statements are then stored in the Comparative Statements 130. In this way, the textual comparisons found in the Corpus 115 are organized and represented in the Storage 220.

In the illustrated embodiment, the Interpretation Component 240 retrieves these Comparative Statements 130 and performs logical interpretation or sentiment analysis on them. In one embodiment, the Interpretation Component 240 classifies each Comparative Statement 130 as positive, negative, or neutral, with respect to each pair of involved therapies or treatments. For example, if the statement is that "treatment A led to better results than treatment B," the Interpretation Component 240 can determine that the comparison is positive with respect to treatment A, and negative with respect to treatment B. Similarly, if the statement is "treatments C and D were both inferior to treatment E," the Interpretation Component 240 determines that, as between therapies C and D, the sentiment is "neutral" or equal. However, as between treatment E and treatments C and D, the sentiment is positive. In this way, the Interpretation Component 240 determines the efficacy of each therapy, as compared to one or more other therapies in the statement.

In one embodiment, the Interpretation Component 240 also generates RESs 140 based on this analysis, as discussed below in more detail. That is, in an embodiment, the Interpretation Component 240 generates an organized and defined data structure that includes the relevant information from the textual Comparative Statement 130. In some embodiments, the Interpretation Component 240 generates a single RES 140 for each Comparative Statement 130. For example, in such an embodiment, if the sentiment is that treatment A is better than treatment B, the Interpretation Component 240 will generate a RES 140 indicating that treatment A is positive with respect to treatment B. In some embodiments, the Interpretation Component 240 also generates a second RES 140 indicating that treatment B is negative with respect to treatment A.

In the illustrated embodiment, the Knowledge Graph Component 110 generally retrieves the RESs 140 from Storage 220, and generates one or more knowledge graphs.

As illustrated, the Knowledge Graph Component 110 includes an Efficacy Evaluator 245, and a Graph Generator 250. Although depicted as discrete components for illustration, in embodiments, the operations and functionality of the Efficacy Evaluator 245 and Graph Generator 250 can be combined or divided across any number of components. Further, although depicted as software components residing in Memory 215, in embodiments, the operations and functionality of the Efficacy Evaluator 245 and Graph Generator 250 can be implemented using hardware, software, or a combination of hardware and software. In an embodiment, the Efficacy Evaluator 245 retrieves and evaluates the RESs 140. For example, in one embodiment, the Efficacy Evaluator 245 searches for RESs 140 relating to one or more disorders or therapies that a user or administrator has selected. In other embodiments, the Efficacy Evaluator 245 retrieves and evaluates all available RESs 140. In an embodiment, the evaluation includes determining whether each RES 140 is already included in the knowledge graph.

Additionally, in some embodiments, the Efficacy Evaluator 245 aggregates the RESs 140 as appropriate, to determine an overall relative efficacy for each set of therapies. For example, in one embodiment, the Efficacy Evaluator 245 identifies RESs 140 with the same endpoints (e.g., that involve the same set of therapies) and aggregates them based on their respective weights to generate an overall relative efficacy between the therapies. In an embodiment, the Graph Generator 250 generates, inserts, and updates or refines nodes and edges in the knowledge graph, based on the evaluation provided by the Efficacy Evaluator 245. In some embodiments, the Graph Generator 250 and/or Efficacy Evaluator 245 aggregate the data by identifying all RESs 140 involving the same pair of therapies and including them in the graph, in order to capture all available evidence that compares the therapies without attempting to establish whether one is overall superior to the other.

As illustrated, the Knowledge Gap Component 165 includes a Cohort Evaluator 288, a Knowledge Evaluator 290, and a Ranking Component 292. Although depicted as discrete components for illustration, in embodiments, the operations and functionality of the Cohort Evaluator 288, Knowledge Evaluator 290, and Ranking Component 292 can be combined or divided across any number of components. Further, although depicted as software components residing in Memory 215, in embodiments, the operations and functionality of the Cohort Evaluator 288, Knowledge Evaluator 290, and Ranking Component 292 can be implemented using hardware, software, or a combination of hardware and software.

In an embodiment, the Cohort Evaluator 288 determines information relating to cohorts of patients. In embodiments, a cohort is a group of individuals that share a set of defined attributes. For example, a first cohort may be all individuals that are "male" and "over 65" in age. Of course, in embodiments, the attributes that define the cohort can include significantly more factors or dimensions, and a cohort can be defined as specifically or generally as the user or administrator desires. In some embodiments, the attributes defining a cohort include the disorder or condition that the user (e.g., a healthcare provider) is interested in treating or researching. Of course, in embodiments, the attributes defining each cohort can include many more factors, as well as more complex attributes such as genotype, phenotype, and the like. Generally, attributes that can be used to define a cohort include any type of information that describers the patient, including age, sex, gender, ethnicity, origin, location, symptomology, status, allergies, conditions, and the like.

In one embodiment, the Cohort Evaluator 288 determines the number of patients or individuals included in a given cohort. In some embodiments, this comprises determining the number of individuals or patients who are known to be included in the cohort (e.g., based on evaluating medical records of the patients). In one embodiment, this includes estimating a total number of people that are included in the cohort. In some embodiments, the estimate is limited to a defined area (such as a region, state, or country). In other embodiments, this geographic limitation is reflected in the attributes used to define the cohort.

In some embodiments, the Cohort Evaluator 288 also analyzes the existing literature (e.g., one or more knowledge graphs) to determine a prognosis for a specified cohort. For example, in such an embodiment, the Cohort Evaluator 288 can identify factors relating to how a patient suffering from a particular disorder is likely to progress, including survival, progression of symptoms, overall well-being, potential physical and mental changes, and the like. In some embodiments, the Cohort Evaluator 288 determines an average or expected prognosis for the typical patient included within the specified cohort. For example, the Cohort Evaluator 288 may evaluate literature or a knowledge graph to determine if any published articles or papers state the prognosis. In some embodiments, the user can specify which particular outcome or outcome type they are most interested in, when determining the expected prognosis. In one embodiment, determining the prognosis of the cohort is based at least in part on the efficacy of the "best" therapy found for the cohort in the knowledge graph.

In one embodiment, the Cohort Evaluator 288 can additionally identify closely-related or similar cohorts to a specified cohort. For example, if a user specifies attributes of "male" and "older than 65," the Cohort Evaluator 288 may determine that a cohort of "male" and "over 60" is closely related. In some embodiments, the Cohort Evaluator 288 can generate a similarity measure between cohorts, to determine how closely related the cohorts are. In one embodiment, the identification of related or similar cohorts is also based on evaluating literature or a knowledge graph. For example, the Cohort Evaluator 288 may determine that one or more published documents have indicated that two or more cohorts are closely related, or likely react similarly to a given therapy.

In the illustrated embodiment, the Knowledge Evaluator 290 analyzes one or more knowledge graphs to determine the current state of the collective knowledge in the field, and identify gaps in this understanding. For example, as discussed in more detail below, in one embodiment, the Knowledge Evaluator 290 evaluates the edges in the knowledge graph that indicate a relationship or comparison between therapies. Based on this evaluation, the Knowledge Evaluator 290 can identify areas where additional study would be helpful (e.g., because there are few or no existing comparisons). In this way, the Knowledge Evaluator 290 can generate Knowledge Gaps 175.

Further, in one embodiment, the Knowledge Evaluator 290 evaluates the individual nodes in the knowledge graph (e.g., each corresponding to a therapy or combination of therapies) to determine the expected efficacy of the therapy, with respect to the indicated cohort(s). For example, if a study found that two-thirds of patients saw improved outcomes with respect to symptomology, the corresponding node in the knowledge graph can indicate that two-thirds of individuals in the cohort respond positively to the therapy (with regards to symptomology). In some embodiments, the efficacy can also include an indication as to the magnitude of the effect (e.g., how significantly symptoms improved). Other examples of the determined efficacy can include a length of time that that passed before the patients survived, were cured, or were in remission, and the like.

In the illustrated embodiment, the Ranking Component 292 scores the identified Knowledge Gaps 175 based on a variety of factors, and ranks the scored gaps in order to present an ordered list of potential avenues of study, sorted based on these factors. In various embodiments, the factors considered can include the availability of patients to participate in a theoretical trial, the number of individuals who are likely to be benefited by the trial (e.g., the number of people who may be interested in the therapy if the results are good), the cost of the therapy or trial, the average or expected prognosis of the cohort, the efficacy of current therapies, the amount of knowledge or connectivity that would be added to the knowledge graph by the suggested study, and the like. In some embodiments, users (e.g., potential researchers) can provide weights for the factors, based on how important or interesting the particular factor is to the user.

In the illustrated embodiment, the Client Device 255 includes a Processor 260, a Memory 265, and Storage 270. In the illustrated embodiment, Processor 260 retrieves and executes programming instructions stored in Memory 265 as well as stores and retrieves application data residing in Storage 270. Processor 260 is representative of a single CPU, multiple CPUs, a single CPU having multiple processing cores, and the like. Memory 265 is generally included to be representative of a random access memory. Storage 270 may be a disk drive or flash-based storage device, and may include fixed and/or removable storage devices, such as fixed disk drives, removable memory cards, or optical storage, network attached storage (NAS), or storage area-network (SAN). Via the Network Interface 275, the Client Device 255 can be communicatively coupled with corpuses of documents (such as Corpus 115), Document Processor 205, and the like.

As illustrated, the Memory 265 of the Client Device 255 includes a User Interface 280 for interacting with the Corpus 115 and/or Document Processor 205. In an embodiment, the User Interface 280 includes a graphical user interface (GUI) that lets users or administrators retrieve and review documents in the Corpus 115. In some embodiments, the User Interface 280 also allows the user to select a subset of the Corpus 115 (e.g., via search queries) to be processed by the Document Processor 205.

Although not illustrated, in embodiments, the Cognitive Interpretation Application 105, Knowledge Graph Component 110, and Knowledge Gap Component 165 each provide one or more application programming interfaces (APIs) that allow the user (through the User Interface 280) to control the operations of the components. For example, in an embodiment, the user can use the User Interface 280 and APIs to indicate the set of documents to be analyzed, and to adjust any settings or configurations of the Cognitive Interpretation Application 105. Further, in an embodiment, the User Interface 280 and APIs enable the user to review the Comparative Statements 130 and/or RESs 140. Additionally, in an embodiment, the User Interface 280 and APIs allow the user to direct the Knowledge Graph Component 110 to generate one or more knowledge graphs based on the RESs 140, and to analyze and parse the generated graphs. Further, in embodiments, the User Interface 280 and APIs associated with the Knowledge Gap Component 165 enable the user to select and weight relevant factors, identify cohorts, and analyze potential trial suggestions based on identified knowledge gaps.

Figure 3A:
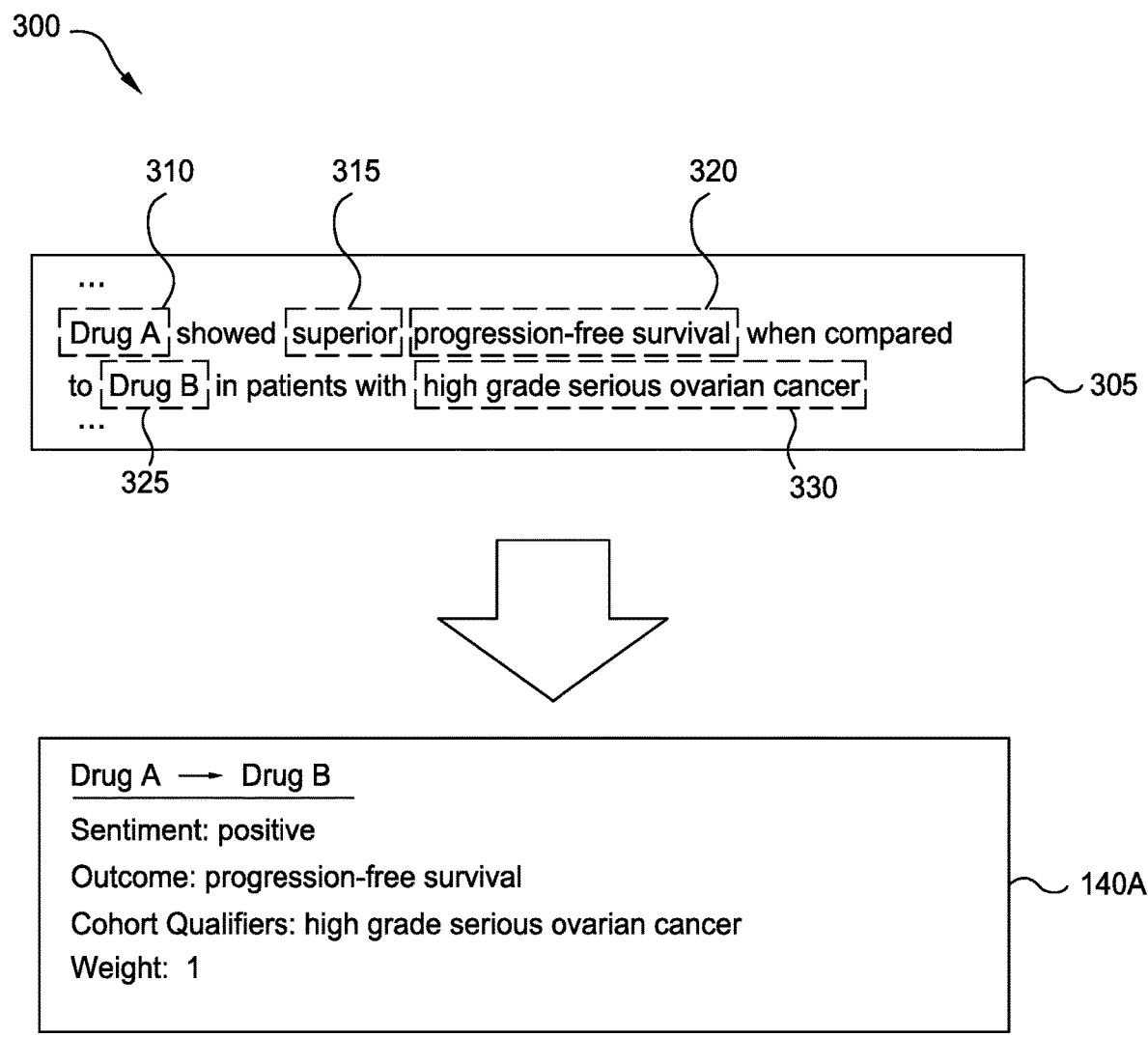
FIG. 3A is a workflow for determining the efficacy for a therapy, as compared to a different therapy, according to one embodiment disclosed herein.

FIG. 3A illustrates a workflow 300 for determining the efficacy for a therapy, as compared to a different therapy, according to one embodiment disclosed herein. In the illustrated workflow 300, a comparative statement (included in an Excerpt 305) is annotated with Annotations 310, 315, 320, 325, and 330. As illustrated by the ellipses above and below the comparative statement, the original document can be any size or length. In an embodiment, the Excerpt 305 was extracted from a document (e.g., by the Extraction Component 230) based on determining that it included a comparative statement.

In the illustrated embodiment, the Excerpt 305 was annotated by the Annotation Component 235, using one or more NLP techniques. As illustrated, Annotations 310 and 325 indicate the therapies mentioned or implicated by the statement. In one embodiment, these therapies are identified based on identifying the subject and object of the statement. Further, as illustrated, the Annotation 320 indicates the outcome (also referred to as the type) that is relevant to the statement. That is, in the illustrated embodiment, the Excerpt 305 discusses the relative efficacy of Drug A and Drug B, with respect to progression-free survival. Additionally, the Annotation 315 indicates the comparator (also referred to as qualifier or type qualifier), which indicates the comparison or statement being made (e.g., that the outcome, progression-free survival, was "superior."). Finally, as illustrated, the Annotation 330 corresponds to the cohort (or cohort qualifier) that the statement applies to.

In the illustrated embodiment, each of the relevant factors (e.g., Annotations 310, 315, 320, 325, and 330) are included within the same Excerpt 305. In embodiments, however, one or more of the relevant pieces of information can be located outside of the Excerpt 305. For example, in an embodiment, the cohort may be specified elsewhere in the document, and not explicitly given in the Excerpt 305. Similarly, one or more of the therapies or outcomes can be given elsewhere. For example, suppose the statement included "therapy Y led to the best results for the patients included in this study." In such an embodiment, the Extraction Component 230 and/or Annotation Component 235 can look elsewhere to determine the other therapy, the cohort, and the particular outcome type. Further, in an embodiment, the excerpt may only summarize one of the therapies in question and the Annotation Component 235 may look elsewhere to determine the complete definition of the therapy. For example, an excerpt may refer to "drug X-based therapy," where all of the components of this therapy are defined elsewhere in the document.

For example, the other therapies being tested may be listed in an introductory section, the cohort can be determined based on analyzing the patients involved, and the outcome of interest can be identified based on other sections of the document. In some embodiments, if the relevant information is not contained within the Excerpt 305, the confidence or weight of the comparative statement is reduced. In some embodiments, the Extraction Component 230 and/or Annotation Component 235 identify both the cohort (e.g., the patient population being studied) as well as cohort qualifiers (e.g., additional restrictions or limitations defining the group to whom the comparison is relevant). In one embodiments, the relevant cohort can identified based on other portions of the document (e.g., based on the abstract or study definitions). For example, a section of the document can indicate that the patients studied included females, aged 65-80, with hypertension. Additionally, the cohort qualifier ("high grade serious ovarian cancer") further restricts or limits the cohort to which the comparison is applicable.

As illustrated, the Cognitive Interpretation Component 105 (e.g., the Sentiment Component 240) then generates a RES 140A, based on the comparative statement. In the illustrated embodiment, as indicated by the arrow from Drug A to Drug B, the RES 140A indicates the relative efficacy of Drug A, as compared to Drug B. As illustrated, the sentiment is "positive," indicating that Drug A is better than Drug B with respect to the indicated cohort and the indicated outcome. Further, as illustrated, the outcome is "progression-free survival," and the cohort is individuals with "high grade serious ovarian cancer." As discussed above, in embodiments, this cohort can include additional attributes or definition, in combination with the cohort qualifiers found in the statement. Additionally, in the illustrated embodiment, the RES 140A includes a weight. In embodiments, this weight is based on a variety of factors, including the confidence of the NLP, the publication characteristics of the document, and the like.

Figure 3B:
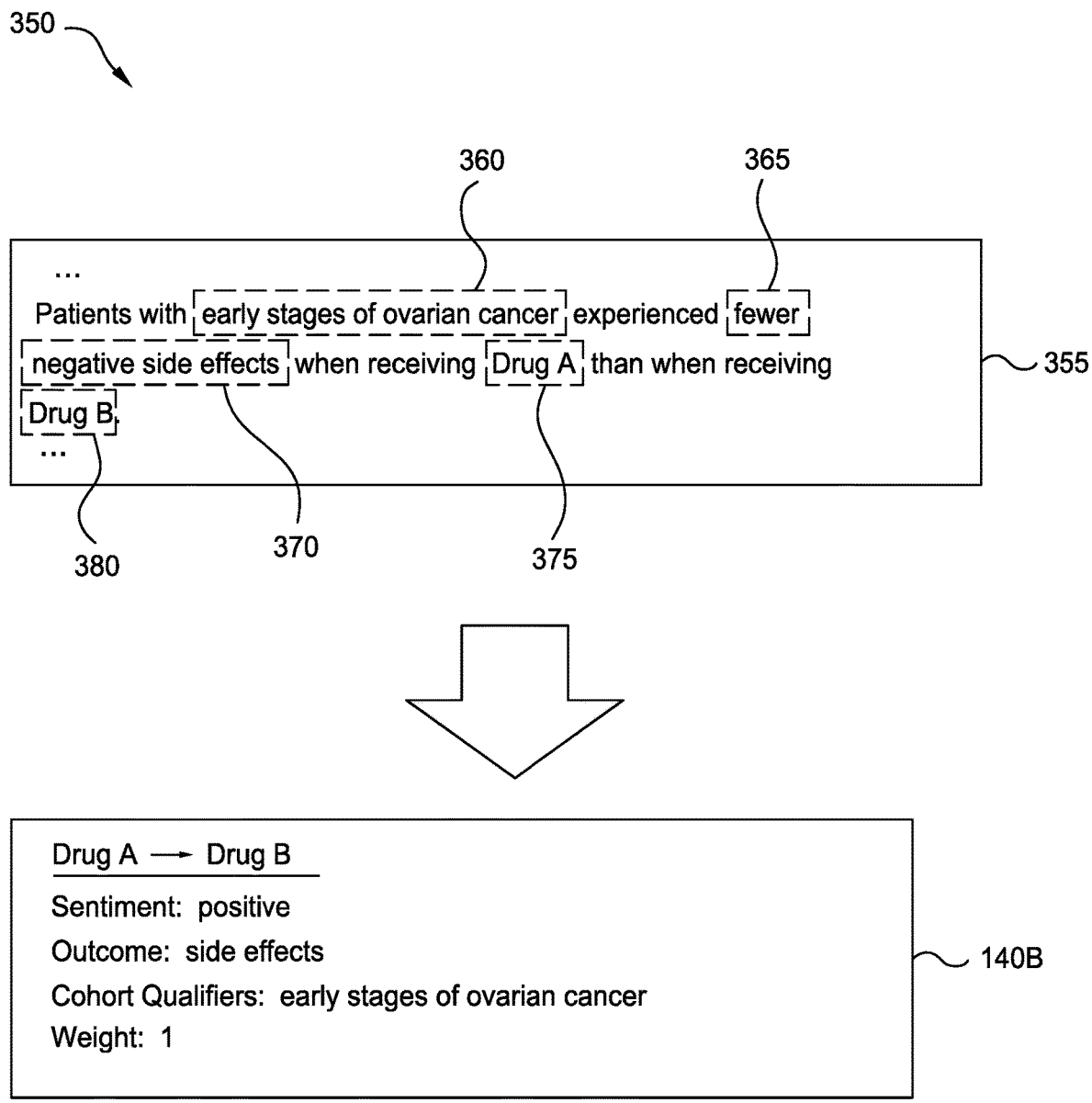
FIG. 3B illustrates a workflow for determining the efficacy for a therapy, as compared to a different therapy, according to one embodiment disclosed herein.

FIG. 3B illustrates a workflow 350 for determining the efficacy for a therapy, as compared to a different therapy, according to one embodiment disclosed herein. In the illustrated workflow 350, a comparative statement (included in an Excerpt 355) is annotated with Annotations 360, 365, 370, 375, and 380. As illustrated by the ellipses above and below the comparative statement, the original document can be any size or length. In an embodiment, the Excerpt 355 was extracted from a document (e.g., by the Extraction Component 230) based on determining that it included a comparative statement.

In an embodiment, the Excerpt 355 was annotated by the Annotation Component 235, using one or more NLP techniques. In the illustrated embodiment, Annotations 375 and 380 indicate the therapies mentioned or implicated by the statement. In one embodiment, these therapies are identified using the NLP models or techniques. Further, as illustrated, the Annotation 370 indicates the outcome of interest (also referred to as the type) that is relevant to the statement. That is, in the illustrated embodiment, the Excerpt 355 discusses the relative efficacy of Drug A and Drug B, with respect to negative side effects. Additionally, the Annotation 365 indicates the comparator (also referred to as qualifier or type qualifier), which indicates the comparison or statement being made (e.g., that the outcome, negative side effects, was "fewer."). Finally, as illustrated, the Annotation 360 corresponds to the cohort (or cohort qualifier) that the statement applies to.

As illustrated, the Cognitive Interpretation Component 105 (e.g., the Sentiment Component 240) then generates a RES 140B, based on the comparative statement. In the illustrated embodiment, as indicated by the arrow from Drug A to Drug B, the RES 140B indicates the relative efficacy of Drug A, as compared to Drug B. As illustrated, the sentiment is "positive," indicating that Drug A is better than Drug B with respect to the indicated cohort and the indicated outcome. That is, because the outcome itself is negative, the Sentiment Component 240 determines that a "worse" result in terms of the number or magnitude of side effects is, in fact, a positive result. Further, as illustrated, the outcome is "toxicity," and the cohort is individuals with "early stages of ovarian cancer." Additionally, in the illustrated embodiment, the RES 140B includes a weight. In embodiments, this weight is based on a variety of factors, including the confidence of the NLP, the publication characteristics of the document, and the like.

Figure 4:
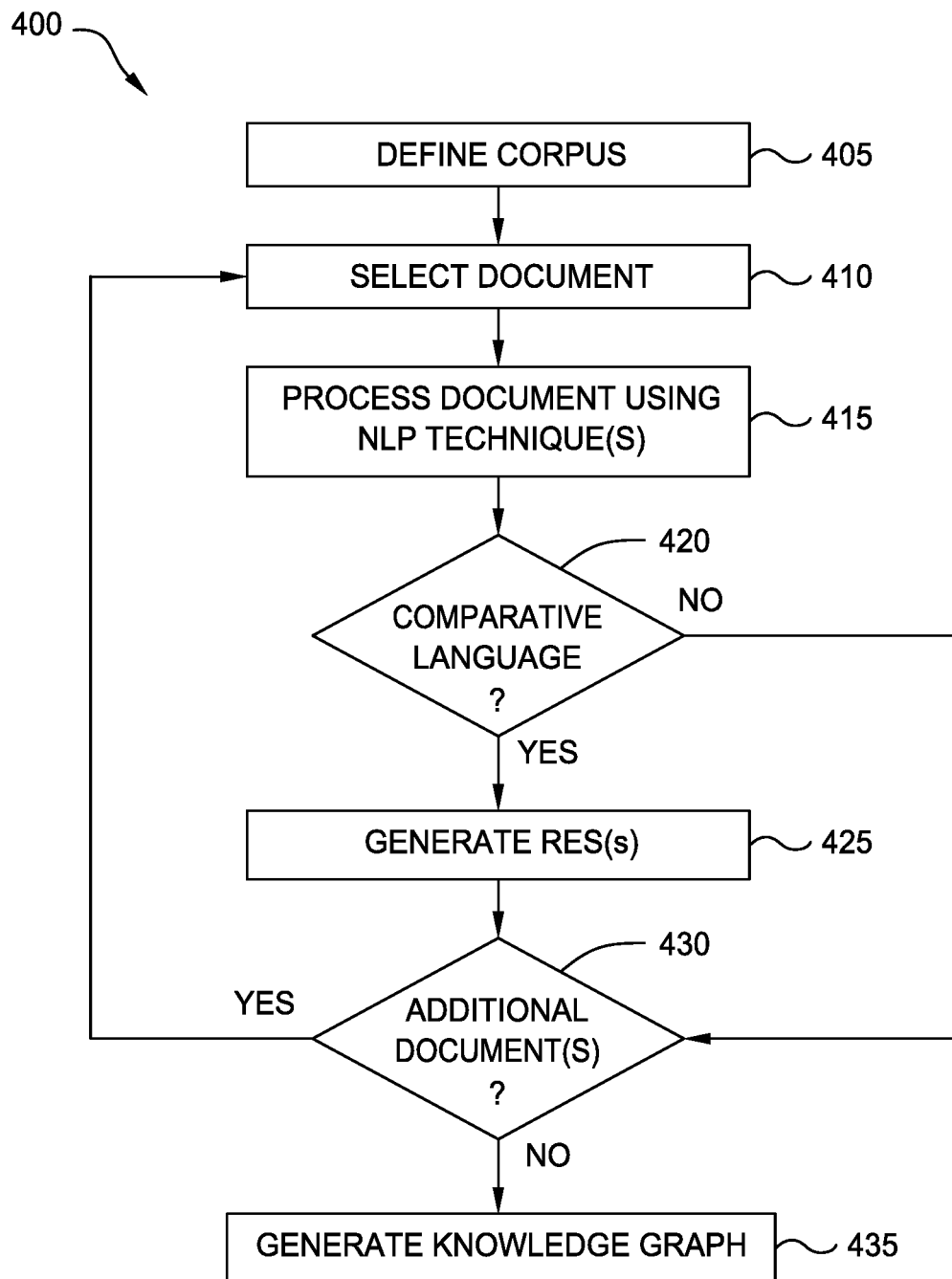
FIG. 4 illustrates a flow diagram illustrating a method for determining relative efficacies of various therapies, according to one embodiment disclosed herein.

FIG. 4 is a flow diagram illustrating a method 400 for determining relative efficacies of various therapies, according to one embodiment disclosed herein. The method 400 begins at block 405, where the Cognitive Interpretation Application 105 defines the relevant corpus. In one embodiment, this is based on a corpus indicated by the user or administrator. In some embodiments, the Cognitive Interpretation Application 105 receives one or more search terms, and builds the relevant corpus by searching or querying a larger corpus based on the search terms. In some embodiments, the Cognitive Interpretation Application 105 determines a set of documents in the identified corpus or sub-corpus that have not yet been processed or ingested. For example, in one embodiment, a user can indicate a disorder or search term, and the Cognitive Interpretation Application 105 can first identify documents relating to the indicated terms, and then identify documents in the corpus that have not already been processed and ingested. In this way, the Cognitive Interpretation Application 105 can selectively analyze new documents in order to update and refine the knowledge base. Once the relevant corpus has been defined, the method 400 proceeds to block 410.

At block 410, the Cognitive Interpretation Application 105 selects a document from the corpus. At block 415, the Cognitive Interpretation Application 105 processes the all or a portion of the selected document using one or more NLP techniques. As discussed above, in some embodiments, the Cognitive Interpretation Application 105 analyzes specified portions of each document. In some embodiments, if no comparisons are found (or if one or more identified comparative statements are missing information or detail), the Cognitive Interpretation Application 105 can process additional sections or text. In one embodiment, the Cognitive Interpretation Application 105 also annotates the extracted excerpts during block 415. The method 400 then proceeds to block 420.

At block 420, the Cognitive Interpretation Application 105 determines whether the selected document (or the portion that was analyzed) includes any comparative statements. If so, the method 400 continues to block 425. If not, the method 400 proceeds to block 430. At block 425, the Cognitive Interpretation Application 105 generates one or more RESs 140 for each of the identified comparative statements found. The method 400 then continues to block 430. At block 430, the Cognitive Interpretation Application 105 determines whether there is at least one additional document in the corpus that is yet to be processed. If so, the method 400 returns to block 410. Otherwise, the method 400 continues to block 435, where the Knowledge Graph Component 110 generates (or updates) a knowledge graph.

Figure 5:
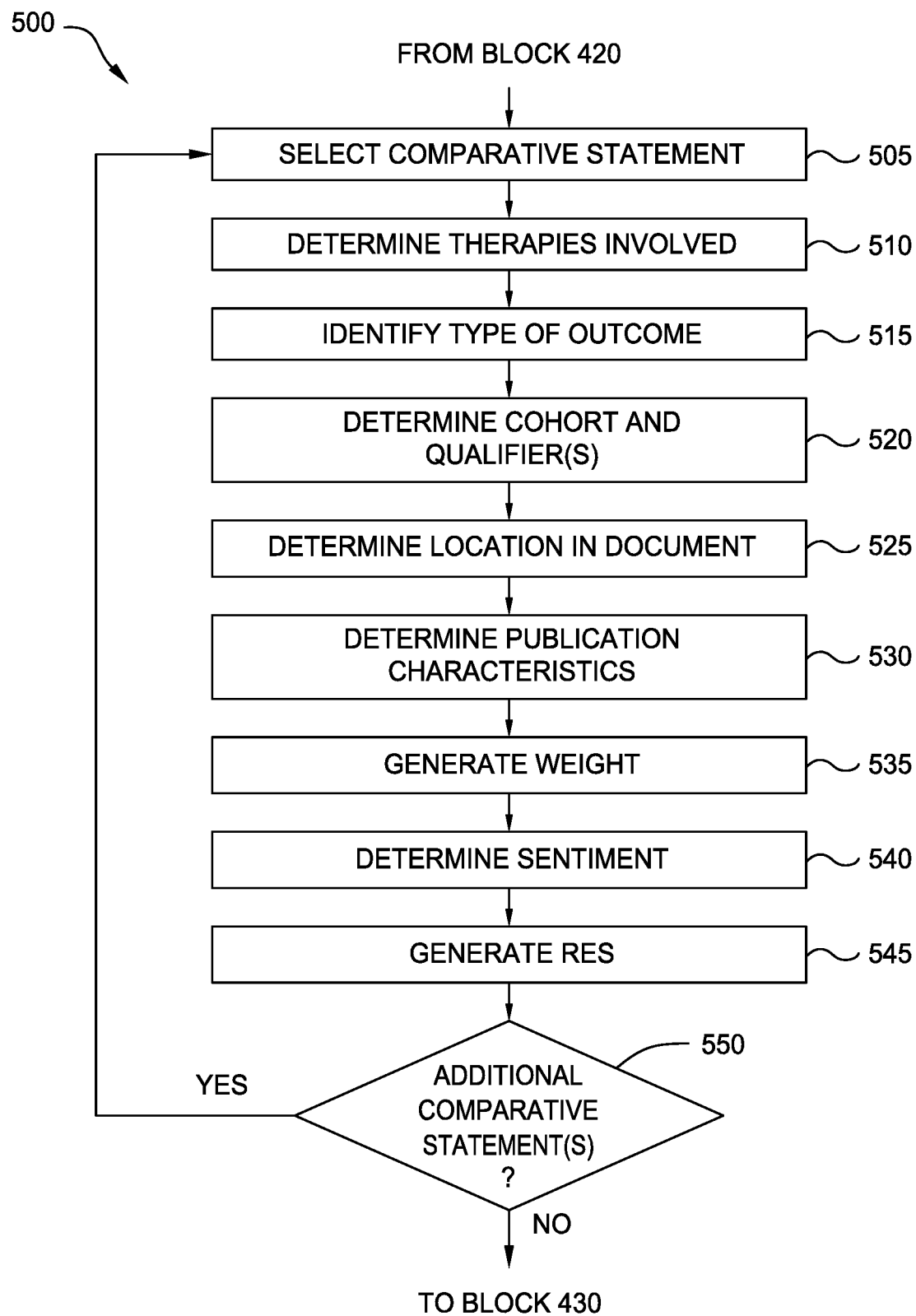
FIG. 5 is a flow diagram illustrating a method for generating relative efficacy structures summarizing comparisons between therapies, according to one embodiment disclosed herein.

FIG. 5 is a flow diagram illustrating a method 500 for generating RESs 140 summarizing comparisons between therapies, according to one embodiment disclosed herein. In one embodiment, the method 500 provides additional detail for block 425 in FIG. 4. The method 500 begins at block 505, where the Cognitive Interpretation Application 105 selects one of the comparative statements that were identified in the selected document. At block 510, the Cognitive Interpretation Application 105 identifies the therapies that are implicated by the selected statement. In one embodiment, the Cognitive Interpretation Application 105 utilizes NLP techniques to identify the relevant therapies. As discussed above, in some embodiments, the Cognitive Interpretation Application 105 parses other sections of the document, and/or other documents and data, in order to disambiguate any unknown or uncertain terms (e.g., ambiguous phrases or acronyms). The method 500 then continues to block 515.

At block 515, the Cognitive Interpretation Application 105 identifies the type of outcome the statement is addressing. That is, the Cognitive Interpretation Application 105 determines the particular outcome or effect that the selected statement is referring to. For example, in a medical embodiment, the outcomes can include overall survival, progression-free survival, remission, cure, death, complications, side effects, and the like. The method 500 then continues to block 520, where the Cognitive Interpretation Application 105 determines the cohort and/or cohort qualifiers that are relevant to the statement. For example, the cohort may be determined based on the patients being studied (e.g., as indicated by criteria used by the study authors when enrolling patients), and the cohort qualifiers can include any additional limitations included in the statement (e.g., "only patients above 65 saw a significant improvement.").

At block 525, the Cognitive Interpretation Application 105 determines the location in the selected document where the selected comparative statement was found. In one embodiment, block 525 comprises determining the section that the statement was in. In an embodiment, the sections are identified based on defined headings, metadata tags, and the like. In some embodiments, the weight of the generated RES 140 is adjusted based on the location. That is, in one embodiment, each section is associated with a respective weight or scale. For example, in one embodiment, the conclusion and abstract sections may be afforded higher weight than the general discussion section.

The method 500 then continues to block 530, where the Cognitive Interpretation Application 105 determines publication characteristics of the selected document that the statement was found in. For example, in one embodiment, the publication characteristics include a date when the document was published, the identity of the publisher, whether it has been peer-reviewed, and the like. In some embodiments, the publication characteristics also include the location in the document where the comparative statement was found. At block 535, the Cognitive Interpretation Application 105 generates a weight for the RES 140 based on the publication characteristics, and/or the determined location. In some embodiments, the Cognitive Interpretation Application 105 also considers any confidence values generated by the NLP models when parsing the text. Further, in one embodiment, the weight is based in part on the strength of the comparator used (e.g., whether the treatment is "slightly better" or "far superior").

The method 500 then continues to block 540, where the Cognitive Interpretation Application 105 determines the sentiment of the statement. In an embodiment, as discussed above, the Cognitive Interpretation Application 105 utilizes NLP to classify the statement as positive, negative, or neutral. Finally, at block 545, the Cognitive Interpretation Application 105 generates a RES 140 for the selected comparative statement based on the determined attributes, sentiment, and weight. At block 550, the Cognitive Interpretation Application 105 determines whether there is at least one additional comparative statement found in the document. If so, the method 500 returns to block 505. Otherwise, the method 500 terminates.

Figure 6:
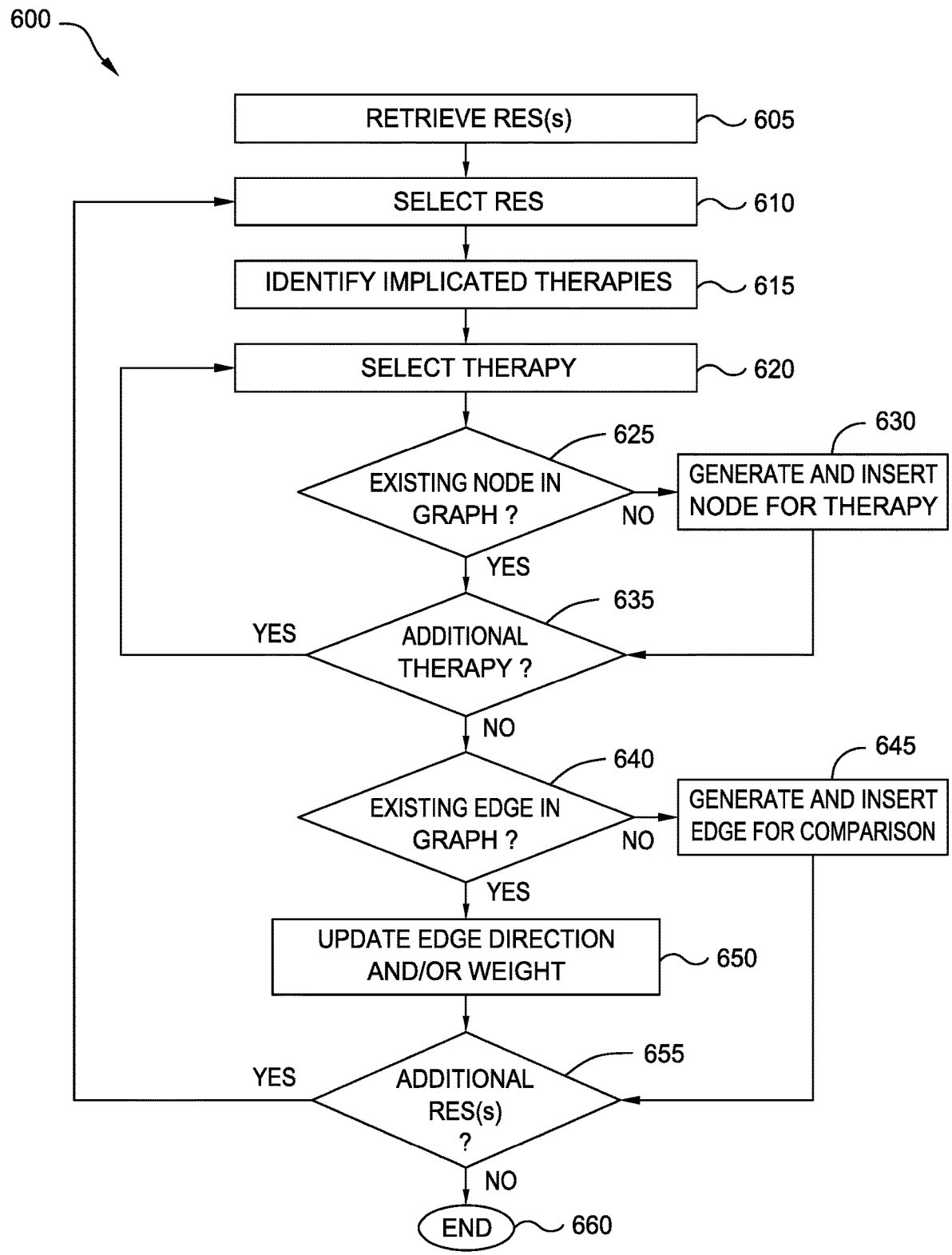
FIG. 6 is a flow diagram illustrating a method for generating a knowledge graph based on generated relative efficacy structures, according to one embodiment disclosed herein.

FIG. 6 is a flow diagram illustrating a method 600 for generating a knowledge graph based on generated relative efficacy structures, according to one embodiment disclosed herein. The method 600 begins at block 605, where the Knowledge Graph Component 110 retrieves one or more RES(s) 140 that were generated by the Cognitive Interpretation Application 105. At block 610, the Knowledge Graph Component 110 selects one of the RESs 140. The method 600 then proceeds to block 615, where the Knowledge Graph Component 110 identifies the therapies that are indicated by the selected RES 140. That is, the Knowledge Graph Component 110 determines which therapies are compared in the RES 140. At block 620, the Knowledge Graph Component 110 selects one of these identified therapies.

The method 600 continues to block 625, where the Knowledge Graph Component 110 determines whether there is an existing node in the knowledge graph for the selected therapy. As discussed above, in an embodiment, each node in the knowledge graph corresponds to a therapy. In some embodiments, a therapy can include a combination of treatments or mediations (e.g., a drug as well as physical therapy). If the selected therapy is already represented in the knowledge graph, the method 600 continues to block 635. If the selected therapy is not yet in the knowledge graph, the method 600 proceeds to block 630, where the Knowledge Graph Component 110 generates and inserts a new node into the graph to represent the selected therapy. The method 600 then continues to block 635.

At block 635, the Knowledge Graph Component 110 determines whether there are additional therapies in the selected RES 140. If so, the method 600 returns to block 620. Otherwise, the method 600 continues to block 640. In the illustrated embodiment, the Knowledge Graph Component 110 analyzes each therapy, and generates new nodes for each. In some embodiments, the knowledge graph is already constructed using a known or defined set of therapies. In such an embodiment, the Knowledge Graph Component 110 does not generate and insert new nodes. In some embodiments, in addition to an existing set of therapies, the Knowledge Graph Component 110 can further generate and insert nodes representing new therapies or new combinations of treatments that are identified in the RES 140.

In one embodiment, each node in the knowledge graph can be connected to zero or more other nodes, based on whether a comparison has been identified between the corresponding therapies. For example, in one embodiment, if two therapies have not been directly compared in the published literature, there will be no link or connection between the corresponding nodes. If, however, the therapies have been compared at least once, there will be an edge or connection between them. In some embodiments, each edge includes a number of dimensions indicating the directionality, the cohort(s) the edge applies to, the outcome(s) the edge applies to, and the like. For example, in such an embodiment, an edge may indicate that treatment A is better than treatment B, with respect to overall survival, in patients over 65. For patients under 65, however, there may be no edge or connection (if the therapies have not been compared for patients under 65), or there may be a link indicating that treatment B is better than treatment A. Similarly, with respect to a different outcome (such as progression-free survival or side effects), there may be no link, or a different link or connection may indicate that treatment B is better than treatment A. In some embodiments, the knowledge graph is constructed with a single edge connecting each pair of therapies, where that edge identifies all documents and/or RESs 140 that included a statement comparing the respective therapies. In another embodiment, the graph can include a respective edge to represent each respective RES 140 that is relevant to the respective pair of therapies.

In some embodiments, each edge in the graph is associated with a respective weight. This weight can be based on a variety of factors, including the number of times the relationship has been identified (e.g., the number of RESs 140 associated with the particular edge), the confidence or weight of each of those RESs 140, and the like. In some embodiments, as additional RESs 140 indicate the same relative efficacy (e.g., that one therapy is better than the other), the weight or strength of the edge is progressively strengthened. If, however, a RES 140 indicates the opposite comparison (e.g., that the first therapy is worse than the other), the weight or strength of the edge is reduced. In this way, each connection in the graph indicates an overall relative efficacy of the therapies, along with an associated strength or confidence in the accuracy of the comparison.

At block 640, the Knowledge Graph Component 110 determines whether there is an existing edge in the knowledge graph representing the relationship indicated by the selected RES 140. That is, in an embodiment, the Knowledge Graph Component 110 determines whether there is any link or connection between the identified therapies, with respect to the indicated cohort and outcome, regardless of the directionality of the relationship (e.g., regardless of whether the existing link matches the determined relative efficacy in the RES 140). In an embodiment, there may be any number of connections between the identified therapies with respect to other cohorts or other outcomes. The determination at block 640, however, is specific to the particular cohort and outcome specified in the RES 140.

In some embodiments, a particular RES 140 can include multiple comparisons. For example, if a statement included that treatment A was superior than all known treatments, the Cognitive Interpretation Application 105 can parse or analyze existing literature (or one or more knowledge graphs) to identify known treatments with respect to the disorder, cohort, and outcome. In such an embodiment, the RES 140 can include an indication of each of these known treatments. In other embodiments, a separate RES 140 is created for each of the comparisons (e.g., for each of the known treatments). In an embodiment, if the RES 140 includes comparisons to multiple therapies, the process discussed below (and reflected by blocks 640, 645, and 650) is repeated for each.

If the Knowledge Graph Component 110 determines, at block 640, that there is no edge in the graph representing the comparison, with respect to the identified cohort and outcome, the method 600 continues to block 645, where the Knowledge Graph Component 110 generates and inserts one. In one embodiment, the directionality of the new edge is based on the sentiment reflected in the selected RES 140 (e.g., positive, negative, or neutral). Further, in an embodiment, the initial weight or strength of the new edge is based on the weight or confidence of the RES 140. In this way, the knowledge graph is updated to reflect that the published literature includes a direct comparison between the therapies, and indicates the relative efficacy of the therapies (e.g., based on the directionality of the edge).

If the Knowledge Graph Component 110 determines, at block 640, that an edge already exists for the indicated comparison, with respect to the specified cohort and outcome, the method 600 continues to block 650, where the Knowledge Graph Component 110 updates the weight and/or direction of the identified edge. In some embodiments, the Knowledge Graph Component 110 instead inserts a new edge, depending on the particular design that will be used to represent multiple comparisons between two treatments in the knowledge graph. As discussed above, in one embodiment, this updating includes adjusting the weight of the edge based on the weight and directionality of the selected RES 140. In an embodiment, if the sentiment reflected by the RES 140 is in the same direction as the existing edge (e.g., the RES 140 and the edge agree that one treatment is superior), the weight or strength is increased. If the directions are opposite, the weight is decreased. Similarly, in one embodiment, if the selected RES 140 has a neutral sentiment (indicating that the therapies are equally effective), the weight of the edge is reduced, regardless of which direction it currently points. If the edge is already neutral, a neutral weight or strength can be increased, indicating that there is additional evidence that the therapies are equally effective.

In one embodiment, the amount that the edge strength is changed is dependent on the magnitude of the confidence or weight associated with the RES 140. If the RES 140 is associated with a high weight, the strength of the edge will be adjusted a greater amount than if the weight of the RES 140 was low. In one embodiment, if the weight falls below a predefined threshold (e.g., within a defined distance from zero), the edge is removed from the graph, indicating that there is no medical consensus regarding the relationship or relative efficacy. In other embodiments, the edge is updated to have no direction, reflecting that there is no solid consensus, and results are mixed (e.g., indicating that the comparison has been studied, but that there is no strong evidence supporting either therapy as more effective than the other). In some embodiments, this edge is retained with a low weight or strength, and is assigned a neutral sentiment to indicate that neither therapy is clearly superior to the other.

Similarly, in some embodiments, if an edge is neutral (or close to neutral) and the weight adjustment would cause the weight to be negative, the direction of the edge is switched, indicating a (potentially weak) new consensus that the relative efficacy of the treatments is reversed from the previously-understood comparison. In some embodiments, each edge in the graph is associated with a directionality as well as a weight or strength of the edge (representing the strength of the evidence). The method 600 then proceeds to block 655, where the Knowledge Graph Component 110 determines whether there is at least one additional RES 140 that has not been analyzed and ingested into the knowledge graph. If so, the method 600 returns to block 610 to select a next RES 140. Otherwise, the method 600 terminates at block 660. In this way, the Knowledge Graph Component 110 can update and refine the knowledge graph based on new therapies and studies. In embodiments, the knowledge graph is a multi-dimensional representation of the medical consensus as to relative efficacies of any number of therapies, with respect to any combination of particular cohorts and outcomes. Advantageously, embodiments of the present disclosure enable the graph to be continuously and rapidly updated when new published literature becomes available, such that the knowledge graph represents the most up-to-date and accurate representation possible. Further, because of the high-dimensionality of the graph (e.g., because the relative efficacies differ based on the individual cohort and outcome), the knowledge graph provides additional data that is far more granular, and is not otherwise available to healthcare providers.

In some embodiments, the knowledge graph can be accessed and searched by healthcare providers in order to determine optimal treatments for a particular patient. For example, in an embodiment, the provider can search the knowledge graph (e.g., using the User Interface 280 of the Client Device 255) to identify therapies and/or relative efficacies that are relevant to the cohort to which the patient belongs. That is, in an embodiment, the knowledge graph can be parsed to identify comparisons that are relevant to a patient in a particular cohort (e.g., having a particular set of attributes). In some embodiments, the provider can also filter, sort, or search the knowledge graph based on the desired outcome. In one embodiment, based on these relative efficacies, the therapies can be scored and ranked, in order to identify the most optimal therapy. This allows the provider to make improved decisions with respect to treating the patient.

In some embodiments, the outcomes types are associated with a predefined hierarchy. That is, some outcomes (e.g., progression-free survival) may be considered more important than other outcomes (e.g., side effects), and therefore be weighted more heavily when aggregating the relative efficacies with respect to each outcome in order to determine an overall relative efficacy (e.g., an overall optimal or best therapy, with respect to all outcomes). In such an embodiment, the ranking or scoring of the therapies may take into account the relative efficacies, as well as the importance or weight of the particular outcome. That is, although a first therapy may be the best with respect to side effects, it may be given a lower score than a second therapy that is better with respect to survival.

Although not illustrated, in some embodiments, the Knowledge Graph Component 110 can further generate nodes for which there are no existing comparisons. For example, if a paper or article includes a study of a particular therapy, but does not include any comparison to other therapies, the Knowledge Graph Component 110 can generate a node for the therapy, without necessarily connecting the node to any other therapies. Further, in some embodiments, the Knowledge Graph Component 110 includes an indication as to the efficacy of each therapy. For example, in such an embodiment, the Cognitive Interpretation Application 105 can determine the overall efficacy for each particular therapy, in addition to determine the relative efficacies of therapies, as compared to each other. This information can then be included in the corresponding node in the knowledge graph. In embodiments, the efficacy can include a percentage of patients who the therapy helped, and/or an amount that the therapy helped.

Figure 7:
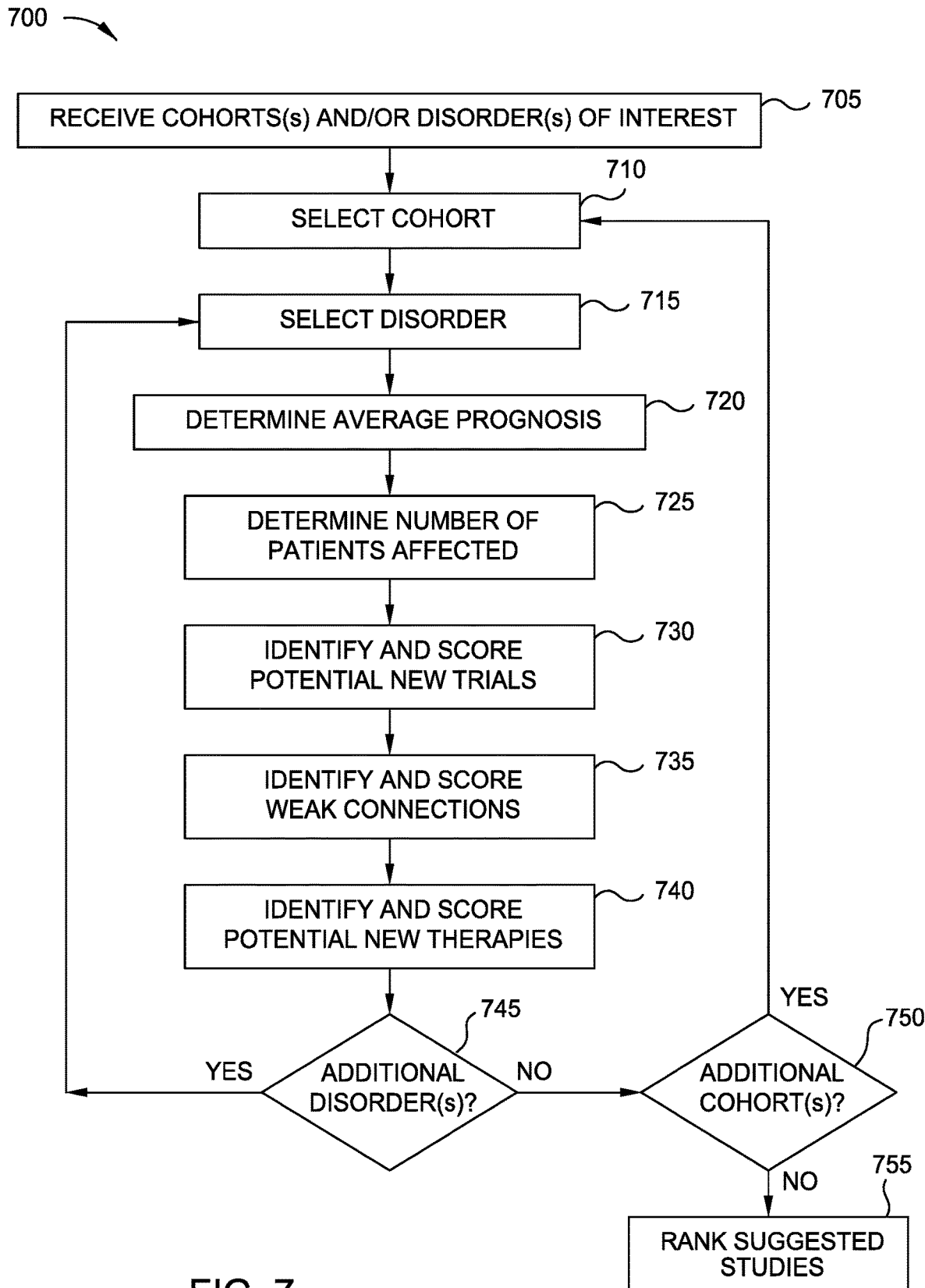
FIG. 7 is a flow diagram illustrating a method for analyzing a knowledge graph to identify knowledge gaps, according to one embodiment disclosed herein.

FIG. 7 is a flow diagram illustrating a method 700 for analyzing a knowledge graph to identify knowledge gaps, according to one embodiment disclosed herein. The method 700 begins at block 705, where the Knowledge Gap Component 165 receives an indication of one or more cohorts, and/or one or more disorders, that are of interest. For example, a user can specify one or more cohorts, one or more disorders, or a combination of cohorts and disorders that they are interested in studying. In some embodiments, the user can also weight or specify preferences (e.g., by specifying weights, or by ordering the provided cohorts and/or disorders) to indicate how interested the user is in studying each. In an embodiment, the final ranking of potential study areas (defined by knowledge gaps) is determined based in part on the weight of the corresponding cohort and/or disorder.

At block 710, the Knowledge Gap Component 165 selects a first cohort from the specified cohorts. In an embodiment, if the user did not specify any cohorts, the Knowledge Gap Component 165 can define its own cohorts for analysis. In one embodiment, the Knowledge Gap Component 165 defines a number of cohorts based on any number of attribute values and/or ranges, and analyzes each. In some embodiments, the Knowledge Gap Component 165 can define the cohorts based on a set of predefined attribute values and/or ranges that can be used to define generic cohorts. For example, in one embodiment, the defined cohorts include respective cohorts for several predefined age groups.

The method 700 then proceeds to block 715, where the Knowledge Gap Component 165 selects a disorder specified by the user. As above, if the user did not specify a disorder, in some embodiments, the Knowledge Gap Component 165 selects from a predefined pool of disorders that may be of interest. In one embodiment, the Knowledge Gap Component 165 identifies disorders that are common for patients included in the selected cohort, and evaluates each. In the illustrated embodiment, a number of cohorts and disorders, in any combination, can be evaluated to identify the cohort/disorder combination that is most promising for future study. Once each combination has been analyzed, the areas are ranked based on a variety of factors, discussed below in more detail.

The method 700 then continues to block 720, where the Knowledge Gap Component 165 determines the average or expected prognosis of an individual in the selected cohort affected by the selected disorder. For example, as discussed above, in one embodiment, the Knowledge Gap Component 165 analyzes existing literature and/or knowledge graphs to determine the likely course of the ailment. In some embodiments, the prognosis includes a number of factors or outcomes, such as overall survival, progression of symptoms, and the like. In one embodiment, the user can specify individual outcomes they are interested in, or a weighting for each. In other embodiments, as discussed above, the outcomes are associated with a predefined hierarchy or weighting based on the importance of each. In some embodiments, this determination is based on how effective the best known therapy is, for the cohort. In other embodiments, the determination is based on how the disorder progresses in the absence of treatment.

At block 725, the Knowledge Gap Component 165 determines the number of patients that are included in the cohort and affected by the disorder. As discussed above, in one embodiment, this step includes determining a number of patients that are available for study or research (e.g., that live in the area and/or have made themselves available for trials). In some embodiments, this step includes determining or estimating a total number of people that are affected in the cohort (e.g., nationwide or worldwide), in order to determine how many individuals could be affected by the results of the study. In some embodiments, the Knowledge Gap Component 165 determines both the number of available study participants, as well as the total number of affected individuals. In this way, the final ranking can be based in part on the ease of conducting the proposed studies (e.g., based on the number of patients who are available locally to participate), as well as the potential number of people whose outcomes could be improved based on the study.

The method 700 then continues to block 730, where the Knowledge Gap Component 165 identifies and scores potential new trials for study. That is, at block 730, the Knowledge Gap Component 165 identifies therapies that have not been directly compared in the published literature (with respect to the selected cohort), and scores each potential comparison based on a variety of factors, as discussed below in more detail with reference to FIG. 8. The method 700 then continues to block 735, where the Knowledge Gap Component 165 identifies and scores weak connections based on the potential that further study can strengthen or clarify the relationship. That is, in the illustrated embodiment, the Knowledge Gap Component 165 identifies connections in the knowledge graph that are relatively weak (e.g., because it has not been studied recently or frequently, or because the existing studies contradict each other) and scores them based on a variety of factors. This is discussed below in more detail with reference to FIG. 9.

The method 700 then proceeds to block 740, where the Knowledge Gap Component 165 identifies and scores potential new therapies. In an embodiment, block 740 includes identifying new therapies that have not been tested with any patients (e.g., with any cohorts). In such an embodiment, the therapies may not be in the knowledge graph at all, or may exist in the graph, but lack a connection to any other therapies. In some embodiments, block 740 includes identifying therapies that have been tested with at least one cohort, but that may be useful for other cohorts that have not yet been tested. Block 740 is discussed in more detail below, with reference to FIG. 10. The method 700 then continues to block 745.

At block 745, the Knowledge Gap Component 165 determines if there is at least one more additional specified disorder that has not been evaluated. If so, the method 700 returns to bock 715. If not, the method 700 continues to block 750, where the Knowledge Gap Component 165 determines whether there is at least one additional cohort that was specified but has not yet been evaluated. If so, the method 700 returns to block 710. Otherwise, the method 700 continues to block 755, where the Knowledge Gap Component 165 ranks the identified studies (e.g., the areas or trials identified and scored in blocks 730, 735, and 740) based on their respective scores. In some embodiments, this final ranking is based in part on the size of the respective cohort, as well as the severity of the respective prognosis. In one embodiment, the ranking is further based on weighting or preferences specified by the user, with respect to the particular cohort, disorder, or domain that the study implicates.

In some embodiments, the final ranking includes potential or suggested studies for a number of different cohorts and/or disorders. As discussed above, in some embodiments, the results can be scored based in part on the number of patients included in the respective cohort, and/or the prognosis of those patients. In this way, the user can easily review the results to determine the most valuable potential studies, based on a wide variety of factors. In one embodiment, the Knowledge Gap Component 165 provides the results for display (e.g., via the User Interface 280) to the user. In some embodiments, the Knowledge Gap Component 165 only provides indications of the suggestions that exceed a predefined threshold score.

In some embodiments, the list of potential or suggested areas of study can be augmented based on ongoing or planned studies. For example, in one embodiment, the Knowledge Gap Component 165 can retrieve a list of planned or ongoing studies and determine whether any of the suggested studies overlap with an ongoing or planned study (e.g., with respect to cohort, disorder, and/or therapies). If so, the score of the suggested study can be reduced to reflect that the knowledge gap may be filled by the ongoing or planned study, such that the suggested study may be less valuable. In one embodiment, the amount that the score is reduced depends in part on the amount of overlap between the suggestion and the planned or ongoing study. In some embodiments, the amount the score is reduced is further based on the timeline of the planned or ongoing study is. For example, if it is in the early planning stages with no clear schedule, the score may be reduced slightly. In contrast, if the study is ongoing and expects to conclude shortly, the score can be reduced significantly.

Figure 8:
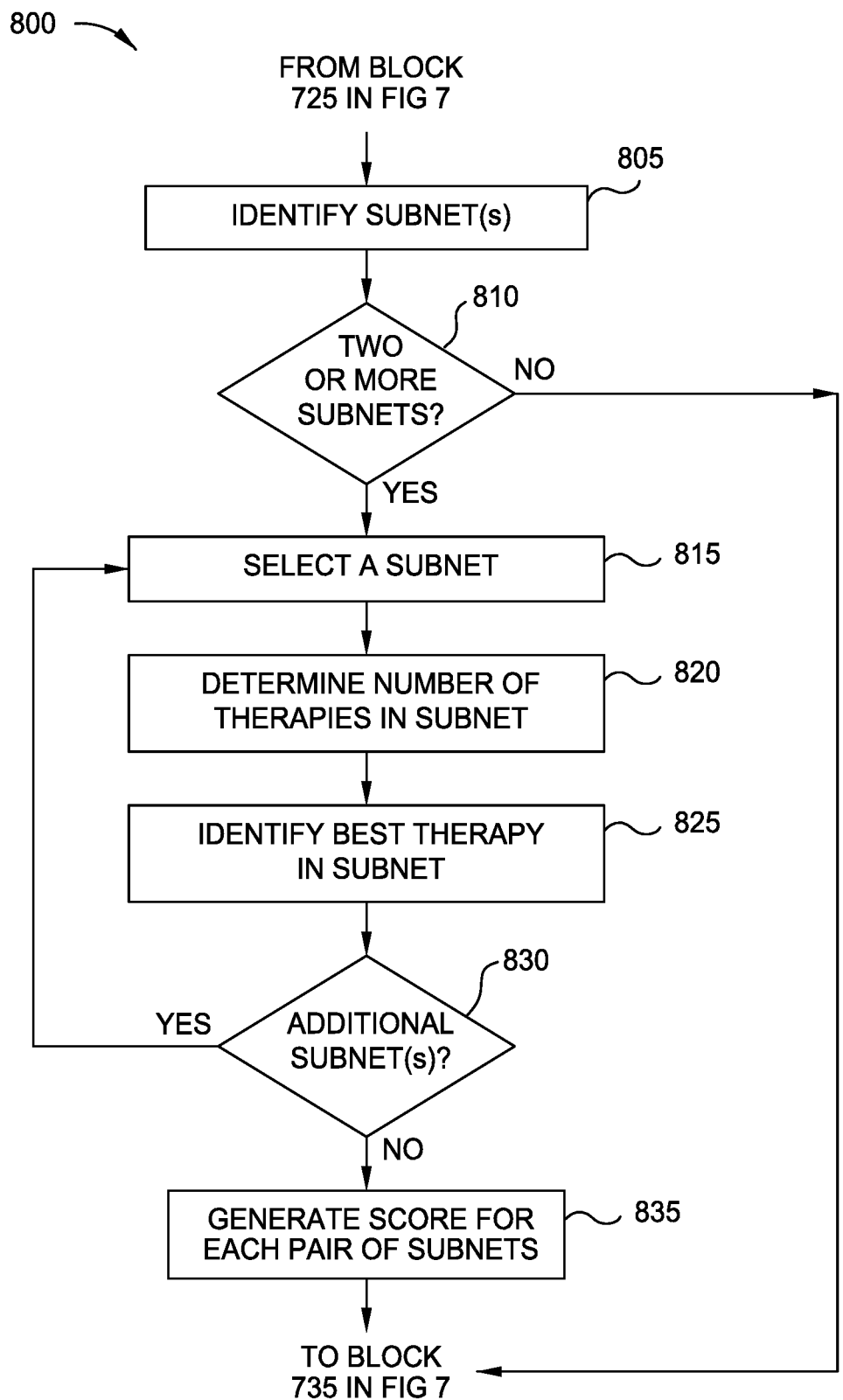
FIG. 8 is a flow diagram illustrating a method for analyzing a knowledge graph to identify potential new studies or comparisons that should be conducted, according to one embodiment disclosed herein.

FIG. 8 is a flow diagram illustrating a method 800 for analyzing a knowledge graph to identify potential new studies or comparisons that should be conducted, according to one embodiment disclosed herein. In an embodiment, the method 800 corresponds to block 730 of FIG. 7. In the illustrated embodiment, the method 800 is used to identify studies that have the potential to connect disparate sections of the knowledge graph. For example, in an embodiment, the knowledge graph includes any number of nodes (each corresponding to a therapy or combination of therapies) and any number of connections among the nodes. In an embodiment, if two therapies (or combinations) have been directly compared, there is a connection or edge between the two corresponding nodes.

In embodiments, in order to determine the relative efficacy of two therapies that have not been directly compared, a sequence of connections or edges can be traversed to determine the likely relative efficacy. For example, suppose Therapy A has been found to be superior to Therapy B, and Therapy B has been found to be superior to Therapy C. Although Therapy A and Therapy C have not been directly compared (and there is no link or edge between the corresponding nodes), it can be inferred that Therapy A is likely better than Therapy C. However, if there is no chain of studies to link the therapies (e.g., if either Therapy A or Therapy C had not been compared to Therapy B), the knowledge graph includes a gap. That is, the two Therapies A and C belong in different subnets or groups which do not have any connections between them to establish relative efficacies of therapies in each, as compared to therapies in the other.

Further, in some embodiments, discrete subnets may exist due to the directionality of the connections. For example, if Therapies A and C are both superior to Therapy B, but Therapies A and C have not been directly compared, it is difficult or impossible to predict or estimate the relative efficacy of Therapy A, as compared to Therapy C. In some embodiments, the Knowledge Gap Component 165 utilizes a number of predefined rules or patterns that are used to identify this type of relationship (or lack thereof). In one embodiment, each subnet corresponds to a set of nodes in the graph (e.g., therapies) that can all be compared with each other, either directly or indirectly, based on known relationships or completed trials reflected in edges in the graph. Further, in one embodiment, two therapies are in different subnets if they cannot be compared, directly or indirectly, based on the edges in the graph. In some embodiments, the Knowledge Gap Component 165 iteratively attempts to compare each pair of therapies in the graph, to determine the subnets.

At block 805, the Knowledge Gap Component 165 identifies these subnets in the knowledge graph, with respect to the selected cohort and disorder. That is, the Knowledge Gap Component 165 utilizes pattern-matching or graph-traversal techniques to identify subnets or sections of the knowledge graph that are either entirely disconnected (e.g., there are no connections or identified comparisons between them) or that are partially disconnected (e.g., the directionality of the connections in the graph prevents comparison between one or more therapies in the first subnet with one or more therapies in the second subnet).

The method 800 then proceeds to block 810, where the Knowledge Gap Component 165 determines if there are at least two subnets in the graph, with respect to the cohort and disorder. If not, the method 800 terminates. That is, if there is only a single subnet (e.g., there are no discontinuities in the graph, with respect to the cohort), the Knowledge Gap Component 165 determines that, with respect to the selected cohort, every known therapy in the knowledge graph can be compared either directly or indirectly to any other therapy. Thus, in an embodiment, the Knowledge Gap Component 165 determines that there are no new trials or studies that would add a useful connection to the knowledge graph. In contrast, if there is at least one such pair of therapies that cannot be compared based on the knowledge graph, (e.g., there are at least two subnets), the method 800 proceeds to block 815. Additionally, in one embodiment, the Knowledge Gap Component 165 identifies therapies with tenuous or sparse connections (e.g., therapies that can be compared, but where the number of edges or connections that must be traversed to make the comparison exceeds a threshold) as potential therapies where additional study could simplify the graph or add useful evidence.

At block 815, the Knowledge Gap Component 165 selects a first of the identified subnets. At block 820, the Knowledge Gap Component 165 determines the number of therapies that are included in the selected subnet. As discussed above, in an embodiment, each subnet corresponds to a set of nodes in the graph (e.g., therapies) that can all be compared with each other, either directly or indirectly, based on known relationships or completed trials. That is, in such an embodiment, if two therapies cannot be compared, they are in different subnets. In one embodiment, the final score generated by the Knowledge Gap Component 165 depends in part on the number of therapies in each subnet, as discussed in more detail below.

The method 800 then proceeds to block 825, where the Knowledge Gap Component 165 identifies the best therapy in the selected subnet. That is, the Knowledge Gap Component 165 evaluates the therapies in the subnet to determine the relative efficacy between each pair (as determined by a direct connection between them, or by two or more connections between them that include other therapies or nodes). Notably, in an embodiment, the Knowledge Gap Component 165 does not determine the actual efficacy of each therapy in order to determine relative efficacies (e.g., in order to determine if the therapies can be compared). That is, in one embodiment, the relative efficacies are determined based on the edges in the graph, which correspond to concrete comparisons made in studies or trials. Thus, in such an embodiment, the Knowledge Gap Component 165 does not determine the actual efficacy of the therapies in order to determine the best therapy. In some embodiments, however, the Knowledge Gap Component 165 can also or alternatively compare therapies based on their actual stated efficacy, even in the absence of an explicit comparison or connection.

In one embodiment, once the best therapy in the subnet is identified, based on the relative efficacies defined by the edges or connections in the knowledge graph, the Knowledge Gap Component 165 also determines the actual efficacy of that best therapy. In some embodiments, the overall ranking for potential new trial between two or more therapies is based in part on the efficacy or quality of the therapies involved, as discussed in more detail below. The method 800 then proceeds to block 830, where the Knowledge Gap Component 165 determines whether there is at least one additional subnet to be analyzed. If so, the method 800 returns to block 815. Otherwise, the method 800 proceeds to block 835.

At block 835, the Knowledge Gap Component 165 generates a score for each pair of subnets in the graph, with respect to the selected cohort. In an embodiment, the score for each pair of subnets is based on the number of therapies in each subnet, as well as the overall efficacy of the best therapy in each subnet. In one embodiment, larger subnets (e.g., subnets that include a higher number of therapies) yield higher scores. That is, because a larger number of therapies would be connected by the suggested study, the potential value for the suggested study is higher. Further, in one embodiment, higher scores are generated if the best therapies in each subnet are fairly good. For example, in such an embodiment, if neither of the best therapies in the subnet pairing are good or effective therapies, there is not likely to be significant value in directly comparing the two. However, if both therapies are effective (as compared to an overall most effective known therapy), there is likely to be significant value in determining which of the two is more effective.

Additionally, in one embodiment, if the therapies have significantly differing efficacies (e.g., a difference above a threshold value), the pairing is given a lower score. That is, because it is likely that nothing of interest will be learned, the suggested study has low potential value. In an embodiment, generating a score for each subnet pairing corresponds to generating a score for a potential trial that compares the best therapies from each subnet in the pairing. In this way, the user can quickly see the actual terms of the suggested study (e.g., the cohort, the therapies to be studied, and the like), as well as an overall score for the study. The method 800 then terminates.

In some embodiments, the Knowledge Gap Component 165 only generates scores for subnet pairings that include a minimum number of therapies. Similarly, in one embodiment, the Knowledge Gap Component 165 generates scores only for subnet pairings where the efficacies of the identified best therapies in each subnet are both above a predefined threshold of efficacy. In this way, the Knowledge Gap Component 165 can avoid generating scores for pairings that are unlikely to be interesting. In other embodiments, however, these pairings are simply assigned a low score, such that they are unlikely to appear near the top of the final ranked list.

Figure 9:
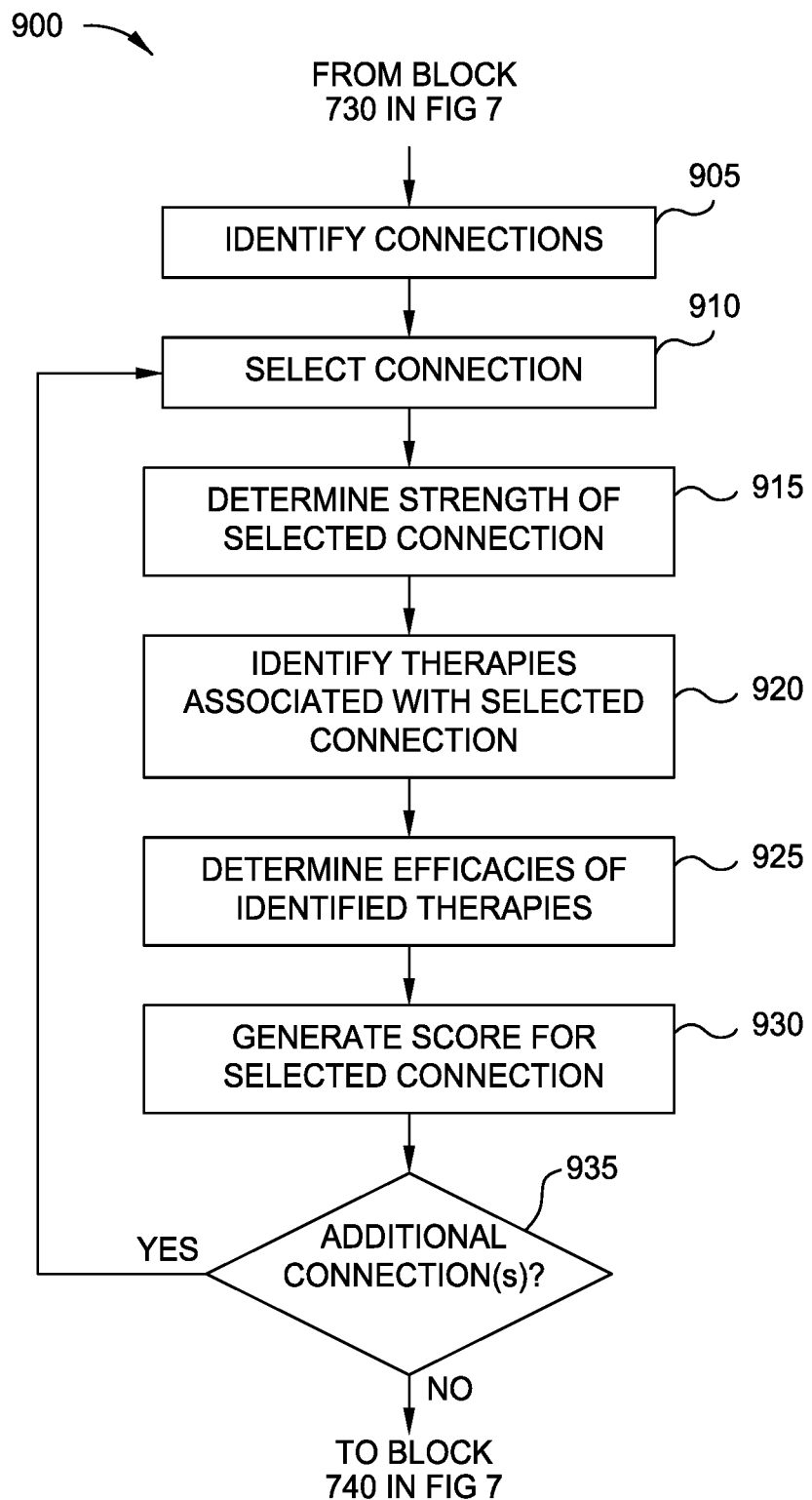
FIG. 9 is a flow diagram illustrating a method for analyzing a knowledge graph to identify conclusions or comparison with weak evidence, according to one embodiment disclosed herein.

FIG. 9 is a flow diagram illustrating a method 900 for analyzing a knowledge graph to identify conclusions or comparison with weak evidence, according to one embodiment disclosed herein. In one embodiment, the method 900 corresponds to block 735 of FIG. 7. In an embodiment, connections can be weak or inconclusive because of a variety of factors, including the number of studies that have involved the comparison, the age of the studies, the prestige or quality of the studies and/or the institutions that performed the studies, and the like. Similarly, in an embodiment, an edge or connection may be weak because the relevant studies have found conflicting results (e.g., some studies found a positive relationship, some found negative, and/or some found no relationship or equal efficacy). As discussed above, in an embodiment, each of these factors is considered by the Knowledge Graph Component 110 when determining the weight for the corresponding edge or connection in the graph.

In some embodiments, these factors are compared to defined thresholds, such that the connection is only evaluated if the thresholds are satisfied. For example, in one embodiment, the Knowledge Gap Component 165 can determine if the number of studies that have been conducted on the relationship or therapies is below a defined threshold. Similarly, in one embodiment, the Knowledge Gap Component 165 can determine whether at least one published document contradicts another, or if a percentage of documents that disagree exceeds a threshold. In some embodiments, however, this determination is made based on the strength or confidence value associated with the connection, as defined by the Knowledge Graph Component 110.

At block 905, the Knowledge Gap Component 165 identifies all of the connections or edges within the knowledge graph that are relevant to the selected cohort and/or disorder. As discussed above, in an embodiment, each connection corresponds to one or more trials, studies, or published documents (e.g., one or more RESs) that include a direct comparison between therapies. The method 900 then proceeds to block 910, where the Knowledge Gap Component 165 selects one of the identified connections. At block 915, the Knowledge Gap Component 165 determines the strength of the selected connection. As discussed above, in an embodiment, each connection in the graph is associated with a strength assigned by the Knowledge Graph Component 110 based on a variety of factors. Thus, in an embodiment, at block 915, the Knowledge Gap Component 165 determines whether the connection or evidence is inconclusive with respect to the selected cohort, based on the strength of the edge. The method 900 then continues to block 920.

In some embodiments, the method 900 only proceeds to block 920 if the determined strength is below a predefined threshold. That is, in such an embodiment, the Knowledge Gap Component 165 can skip connections that are sufficiently strong, because they are unlikely to be interesting for further study with respect to the cohort (e.g., because the published literature has already reached a firm consensus on the relative efficacies of the therapies). In such an embodiment, the method 900 proceeds directly to block 935, to determine whether there are additional connections to be sampled. In other embodiments, however, these strong connections are simply assigned a lower weight, as compared to weak connections.

At block 920, the Knowledge Gap Component 165 identifies the therapies that are associated with the selected connection. That is, the Knowledge Gap Component 165 identifies the nodes at each end of the selected connection, and identifies the therapies associated with those nodes. Next, at block 925, the Knowledge Gap Component 165 determines the actual efficacies of those identified therapies. That is, in an embodiment, the Knowledge Gap Component 165 determines how effective each of the therapies are. In some embodiments, connections between two relatively effective therapies may be more interesting than connections between therapies that are both poor. Similarly, connections between therapies that are significantly different in efficacy are unlikely to be as interesting. Further, in one embodiment, the Knowledge Gap Component 165 only generates a score for the connection if both of the therapies have a minimum threshold level of efficacy, as discussed above. Thus, in an embodiment, the Knowledge Gap Component 165 determines the actual efficacy of each, in order to determine how interesting the connection is (e.g., what the score of the connection should be) in terms of whether the results would be useful or add value to the domain.

The method 900 then proceeds to block 930, where the Knowledge Gap Component 165 generates a score for the selected connection. As discussed above, in one embodiment, the generated score is inversely related to the strength of the connection (e.g., the confidence associated with it). That is, relationships with more evidence (and thus higher strengths or confidence values) are given lower scores, and relationships with less evidence (and thus lower strengths or confidence) are given higher scores. Further, in an embodiment, connections between two therapies that are both effective will be given a higher score than a connection between two ineffective therapies, or a connection between an effective therapy and an ineffective therapy. In this way, the final score reflects how likely it is that the potential new study will add coherence to the knowledge graph (e.g., because the existing evidence is weak), as well as how likely the potential study is to be useful or interesting to actual patients (e.g., because the therapies involved are both believed to be effective, but it is unclear how they differ).

The method 900 continues to block 935, where the Knowledge Gap Component 165 determines whether there is at least one connection remaining in the knowledge graph that has not yet been analyzed. If so, the method 900 returns to block 910. Otherwise, the method 900 terminates. In this way, the Knowledge Gap Component 165 can identify published literature (e.g., trials or studies) that has examined the relationship between two therapies, but where the literature is ambiguous, conflicting, new (e.g., such that it has not yet been reviewed or repeated), old (such that it may no longer be relevant), sparse, or performed by questionable entities. This allows the Knowledge Gap Component 165 to identify comparisons that have already been studied, but that should be repeated or studied further in order to develop the corpus of knowledge.

Figure 10:
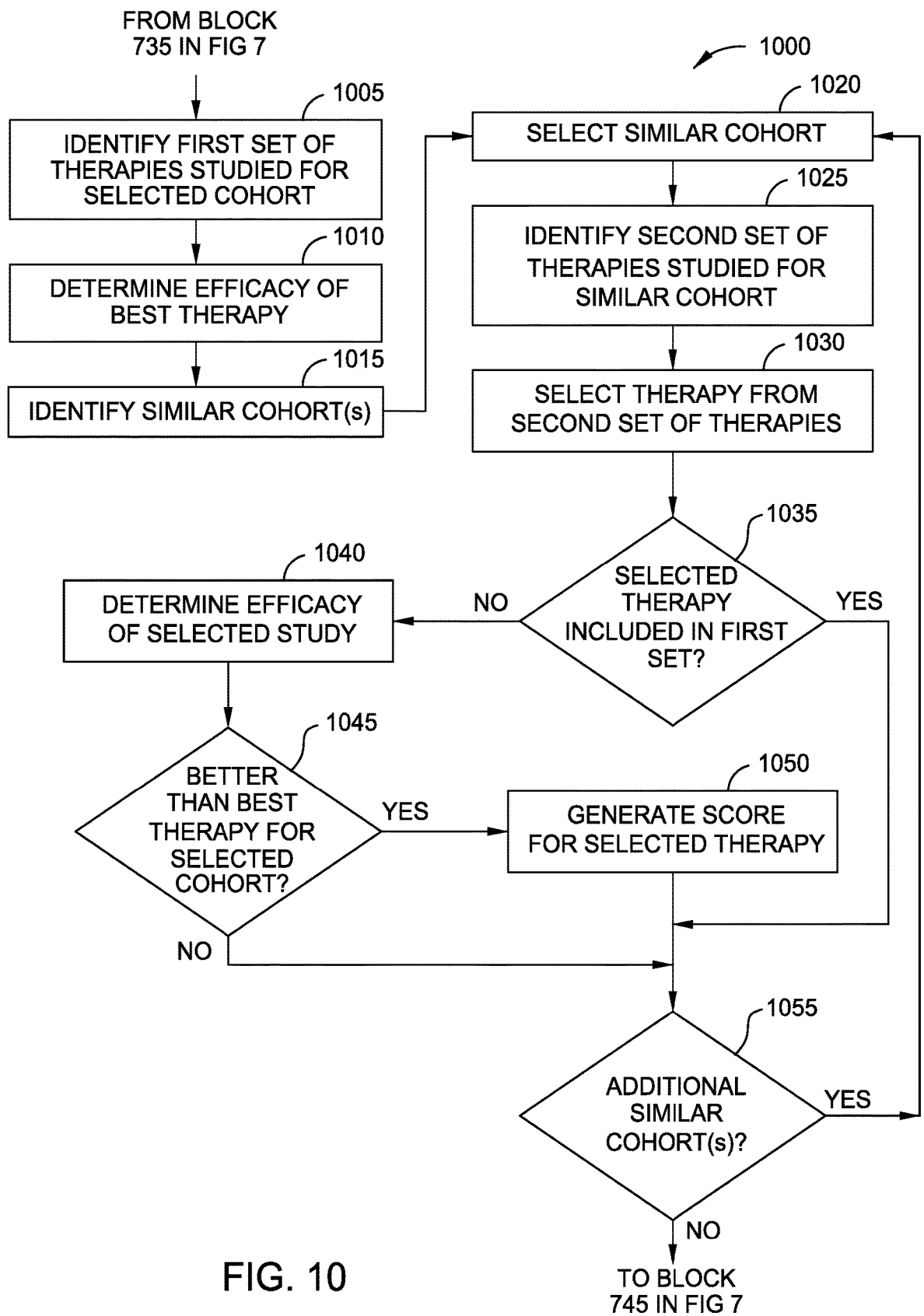
FIG. 10 is a flow diagram illustrating a method for analyzing a knowledge graph to identify potential new therapies, according to one embodiment disclosed herein.

FIG. 10 is a flow diagram illustrating a method 1000 for analyzing a knowledge graph to identify potential new therapies, according to one embodiment disclosed herein. In one embodiment, the method 1000 corresponds to block 740 of FIG. 7. In an embodiment, the method 1000 is utilized to identify cohorts of patients that have not been fully studied. In one embodiment, the method 1000 enables the Knowledge Gap Component 165 to identify cohorts with poor results (e.g., where the best known therapy is inadequate or unsatisfactory). In some embodiments, the Knowledge Gap Component 165 can further identify therapies that have the potential to improve results for the cohort, such that a new study should be conducted to determine the efficacy of the therapy with respect to the cohort. In one embodiment, this identification is based on identifying newly discovered or created therapies and treatments that have not yet been tested with the cohort. In some embodiments, this includes identifying therapies that work well with similar or related cohorts, but that has never been tested with the index cohort.

The method 1000 begins at block 1005, where the Knowledge Gap Component 165 identifies a first set of therapies that have been studied with respect to the selected cohort. That is, the Knowledge Gap Component 165 identifies therapies (e.g., nodes and/or connections) in the knowledge graph where the relevant cohort includes or corresponds to the selected cohort. The method 1000 then proceeds to block 1010, where the Knowledge Gap Component 165 identifies the best therapy for the cohort (based on the connections, or relative efficacies, reflected in the knowledge graph), and determines the actual efficacy of that therapy. In one embodiment, if two or more therapies cannot be compared (e.g., because they are in disconnected subnets), both are selected. In other embodiments, the Knowledge Gap Component 165 estimates which therapy is superior, based on the actual efficacies of each.

In some embodiments, the Knowledge Gap Component 165 compares this efficacy to a threshold to determine whether to proceed with the method 1000, or to terminate it. For example, in such an embodiment, if a highly effective treatment has already been found for the selected cohort, it may unlikely that additional study will yield a better therapy. In other embodiments, the final score is inversely related to the efficacy of the best therapy for the cohort/disorder. That is, in an embodiment, if the cohort and/or disorder already has a satisfactory therapy, it is less interesting and thus will have a lower score than a cohort/disorder combination that has poor therapies (e.g., there are not satisfactory or good options for the cohort). The method 1000 then continues to block 1015.

At block 1015, the Knowledge Gap Component 165 identifies similar cohorts to the selected cohort. In one embodiment, this includes adjusting or expanding the range of one or more attributes used to define the selected cohort, removing one or more of the attributes from consideration, or changing the value of one or more attributes. In some embodiments, the number of attributes that can be changed or removed is set by a user. In one embodiment, the amount that the values or range can differ is similarly defined by the user. In some embodiments, a user can define one or more attributes to be protected (e.g., such that all of the related or similar cohorts must also share those attributes).

In one embodiment, the Knowledge Gap Component 165 can generate similar cohorts based on defined standards or rules relating to cohort similarity. For example, a rule may define that a cohort with a specified age range is "similar" to a cohort with an overlapping age range, or to a cohort with an age range that includes a value within X years of the range specified by the selected cohort. In some embodiments, the Knowledge Gap Component 165 can generate a similarity measure or difference measure between the cohorts, in order to determine their similarity. In an embodiment, this measure is compared to a threshold value (e.g., set by a user) in order to determine whether the cohorts are sufficiently similar to be considered. In one embodiment, the user can manually define one or more related cohorts as well, to help aid this process.

The method 1000 then continues to block 1020, where the Knowledge Gap Component 165 selects an identified similar cohort. At block 1025, the Knowledge Gap Component 165 identifies a set of therapies that have been evaluated with respect to the selected similar cohort. In an embodiment, this process mirrors block 1005. The method 1000 then continues to block 1030, where the Knowledge Gap Component 165 selects a therapy from this identified second set of therapies that are relevant to the second cohort. At block 1035, the Knowledge Gap Component 165 determines whether this selected therapy is also included in the first set of therapies. That is, the Knowledge Gap Component 165 determines whether the therapy has also been studied or evaluated with respect to the originally selected cohort. If so, the method 1000 proceeds to block 1055.

If the selected therapy does not overlap (e.g., it has not been tested with respect to the selected cohort), the method 1000 proceeds to block 1040, where the Knowledge Gap Component 165 determines the actual efficacy of the selected study. That is, the Knowledge Gap Component 165 determines the observed outcomes, and/or percentiles of patients who achieved each outcome. At block 1045, the Knowledge Gap Component 165 determines whether this efficacy is superior to the efficacy of the best therapy identified in block 1010. In one embodiment, as discussed above, the different potential outcomes are associated with differing weights based on a defined hierarchy. In other embodiments, the user can specify weights or preferences for outcomes of interest. In an embodiment, the Knowledge Gap Component 165 can determine an objective comparison between the two therapies based on the percentiles reported for each outcome, in conjunction with the defined weights or hierarchy for each.

If the selected therapy is worse than the best therapy identified for the selected cohort at block 1015, the method 1000 continues to block 1055. That is, because the cohort already has a therapy superior to the identified therapy, it is unlikely that a new study directly testing the therapy for the cohort will be interesting or useful. If, however, the Knowledge Gap Component 165 determines at block 1045 that the new therapy is better than the best therapy known for the selected cohort, the method 1000 proceeds to block 1050, where the Knowledge Gap Component 165 generates a score for the selected therapy.

In one embodiment, the score is based on a variety of factors, including the magnitude of the difference between the therapies (e.g., how much better the selected therapy is, as compared to the best therapy known for the cohort). In such an embodiment, the score is directly related to the magnitude of the difference. Further, in one embodiment, the score is related to the actual efficacy of the therapy selected at block 1030, with respect to the similar cohort. That is, if the therapy is not particularly effective with respect to the similar cohort, it is also probably not particularly effective for the select cohort and is thus given a lower score. In contrast, if the therapy is effective for the similar cohort, it is more likely to be interesting or useful to the selected cohort, and thus is given a higher score. In some embodiments, this score is further based on the similarity of the cohorts, such that therapies associated with more similar cohorts are provided a higher score. Further, in one embodiment the score is based in part on the efficacy of the best therapy known for the cohort, as discussed above. The method 1000 then proceeds to block 1055, where the Knowledge Gap Component 165 determines whether there is at least one additional similar cohort to be analyzed. If so, the method 1000 returns to block 1020. Otherwise, the method 1000 terminates.

Although not illustrated, in one embodiment, after all similar cohorts have been processed, the Knowledge Gap Component 165 determines whether any therapies were identified and scored twice (e.g., for separate similar cohorts). If so, the Knowledge Gap Component 165 can aggregate the entries and adjust the score, such that the same therapy is not presented twice in the list of potential therapies to be tested. In one embodiment, adjusting the score includes aggregating or adding the individual scores. In this way, the Knowledge Gap Component 165 can identify therapies that have proven effective for similar related cohorts, and indicate them to the user. These therapies may be interesting or useful to study with respect to the selected cohort, in order to improve patient outcomes.

Figure 11:
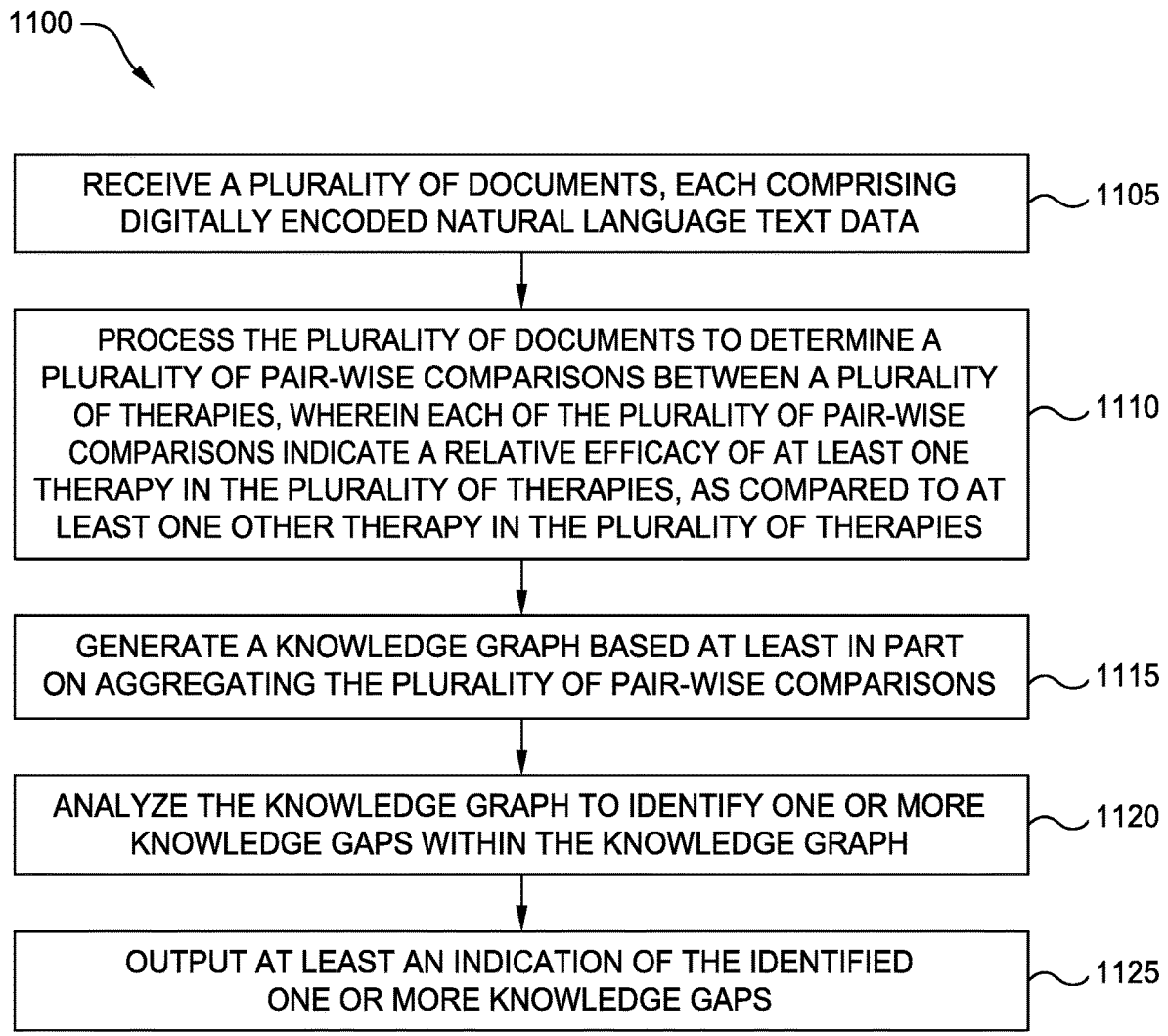
FIG. 11 is a flow diagram illustrating a method for analyzing a knowledge graph to identify knowledge gaps, according to one embodiment disclosed herein.

FIG. 11 is a flow diagram illustrating a method 1100 for analyzing a knowledge graph to identify knowledge gaps, according to one embodiment disclosed herein. The method 1100 begins at block 1105, where a Cognitive Interpretation Application 105 receives a plurality of documents, each comprising digitally encoded natural language text data. At block 1110, the Cognitive Interpretation Application 105 processes the plurality of documents to determine a plurality of pair-wise comparisons between a plurality of therapies, wherein each of the plurality of pair-wise comparisons indicate a relative efficacy of at least one therapy in the plurality of therapies, as compared to at least one other therapy in the plurality of therapies. The method 1100 then proceeds to block 1115, where a Knowledge Graph Component 110 generates a knowledge graph based at least in part on aggregating the plurality of pair-wise comparisons. Additionally, at block 1120, a Knowledge Gap Component 165 analyzes the knowledge graph to identify one or more knowledge gaps within the knowledge graph. Finally, the method 1100 continues to bloc 1125, where the Knowledge Gap Component 165 outputs at least an indication of the identified one or more knowledge gaps.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the preceding, reference is made to embodiments presented in this disclosure. However, the scope of the present disclosure is not limited to specific described embodiments. Instead, any combination of the preceding features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the preceding aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications (e.g., the Cognitive Interpretation Application 105, the Knowledge Graph Component 110, and/or the Knowledge Gap Component 165) or related data available in the cloud. For example, the Knowledge Gap Component 165 could execute on a computing system in the cloud and analyze knowledge graphs to identify gaps in the published literature. In such a case, the Knowledge Gap Component 165 could access and parse knowledge graphs and store indications and scores of those gaps at a storage location in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A method, comprising:
   receiving a plurality of documents, each comprising digitally encoded natural language text data;
   processing the plurality of documents to determine a plurality of pair-wise comparisons between a plurality of therapies, wherein each of the plurality of pair-wise comparisons indicates a relative efficacy of at least one therapy in the plurality of therapies, as compared to at least one other therapy in the plurality of therapies;
   generating a knowledge graph, by operation of one or more processors, comprising aggregating the plurality of pair-wise comparisons, wherein the knowledge graph comprises a multidimensional representation of relative efficacies of the plurality of therapies with respect to a plurality of cohorts and a plurality of outcomes;
   updating the knowledge graph when new published literature becomes available;
   analyzing the knowledge graph to identify one or more knowledge gaps within the knowledge graph;
   generating a score for a first knowledge gap of the one or more knowledge gaps, comprising:
      identifying a cohort associated with the first knowledge gap;
      determining a number of patients in the cohort; and
      identifying a most effective therapy for the cohort; and
   outputting an indication of the identified one or more knowledge gaps and the score for the first knowledge gap.

2. The method of claim 1, wherein analyzing the knowledge graph to identify one or more knowledge gaps within the knowledge graph comprises:
   determining that a first therapy and a second therapy have not been directly compared against each other, in the plurality of documents, with respect to a first cohort.

3. The method of claim 2, wherein analyzing the knowledge graph to identify one or more knowledge gaps within the knowledge graph further comprises:
   determining that an efficacy of the first therapy and an efficacy of the second therapy are both above a predefined threshold efficacy.

4. The method of claim 1, wherein analyzing the knowledge graph to identify one or more knowledge gaps within the knowledge graph comprises:
   determining that an overall relative efficacy of a first therapy, as compared to a second therapy, is inconclusive, based on determining that evidence for the overall relative efficacy does not satisfy one or more defined criteria.

5. The method of claim 4, wherein determining that the overall relative efficacy of the first therapy, as compared to the second therapy, is inconclusive comprises at least one of:
   (i) determining that a number of documents, of the plurality of documents, that have compared the first and second therapies is below a predefined threshold; or
   (ii) determining that a first of the plurality of pair-wise comparisons contradicts a second of the plurality of pair-wise comparisons.

6. The method of claim 1, wherein analyzing the knowledge graph to identify one or more knowledge gaps within the knowledge graph comprises:
   identifying a first subset of the knowledge graph, wherein the first subset is connected by one or more pair-wise comparisons of the plurality of pair-wise comparisons;
   identifying a second subset of the knowledge graph, wherein the second subset is connected by one or more pair-wise comparisons of the plurality of pair-wise comparisons; and
   determining that the first and second subsets of the knowledge graph are disconnected from each other.

7. The method of claim 1, wherein analyzing the knowledge graph to identify one or more knowledge gaps within the knowledge graph comprises:
   analyzing the knowledge graph to determine, for a first cohort, a most effective therapy, based on at least a subset of the plurality of pair-wise comparisons; and
   determining that an efficacy of the most effective therapy is below a predefined threshold.

8. The method of claim 1, wherein processing the plurality of documents to determine the plurality of pair-wise comparisons comprises, for at least a first document in the plurality of documents:
   identifying and extracting, based on identifying comparative language, a conclusion specified within natural language text of the first document, wherein the conclusion comprises a comparison between two or more therapies of the plurality of therapies;
   determining a sentiment of the extracted conclusion, with respect to at least one therapy of the plurality of therapies; and
   identifying one or more cohorts of patients that are associated with the first document.

9. The method of claim 1, wherein generating the knowledge graph comprises:
   identifying a first subset of pair-wise comparisons, from the plurality of pair-wise comparisons by determining that each of the first subset of pair-wise comparisons indicates a first cohort and indicates relative efficacy of a first therapy and a second therapy; and
   aggregating the first subset of pair-wise comparisons to determine an overall relative efficacy of the first therapy with respect to the second therapy.

10. A computer program product comprising a non-transitory computer-readable storage medium having computer-readable program code embodied therewith, the computer-readable program code executable by one or more computer processors to perform an operation comprising:
   receiving a plurality of documents, each comprising digitally encoded natural language text data;
   processing the plurality of documents to determine a plurality of pair-wise comparisons between a plurality of therapies, wherein each of the plurality of pair-wise comparisons indicates a relative efficacy of at least one therapy in the plurality of therapies, as compared to at least one other therapy in the plurality of therapies;
   generating a knowledge graph, by operation of one or more processors, comprising aggregating the plurality of pair-wise comparisons, wherein the knowledge graph comprises a multidimensional representation of relative efficacies of the plurality of therapies with respect to a plurality of cohorts and a plurality of outcomes;
   updating the knowledge graph when new published literature becomes available;

analyzing the knowledge graph to identify one or more knowledge gaps within the knowledge graph; and
generating a score for a first knowledge gap of the one or more knowledge gaps, comprising:
   identifying a cohort associated with the first knowledge gap;
   determining a number of patients in the cohort; and
   identifying a most effective therapy for the cohort; and
outputting an indication of the identified one or more knowledge gaps and the score for the first knowledge gap.

11. The computer program product of claim 10, wherein analyzing the knowledge graph to identify one or more knowledge gaps within the knowledge graph comprises:
   determining that a first therapy and a second therapy have not been compared, in the plurality of documents, with respect to a first cohort; and
   determining that an efficacy of the first therapy and an efficacy of the second therapy are both above a predefined threshold efficacy.

12. The computer program product of claim 10, wherein analyzing the knowledge graph to identify one or more knowledge gaps within the knowledge graph comprises:
   determining that an overall relative efficacy of a first therapy, as compared to a second therapy, is inconclusive based on at least one of:
      (i) determining that a number of documents, of the plurality of documents, that have compared the first and second therapies is below a predefined threshold; or
      (ii) determining that a first of the plurality of pair-wise comparisons contradicts a second of the plurality of pair-wise comparisons.

13. The computer program product of claim 10, wherein analyzing the knowledge graph to identify one or more knowledge gaps within the knowledge graph comprises:
   identifying a first subset of the knowledge graph, wherein the first subset is connected by one or more pair-wise comparisons of the plurality of pair-wise comparisons;
   identifying a second subset of the knowledge graph, wherein the second subset is connected by one or more pair-wise comparisons of the plurality of pair-wise comparisons; and
   determining that the first and second subsets of the knowledge graph are disconnected from each other.

14. The computer program product of claim 10, wherein analyzing the knowledge graph to identify one or more knowledge gaps within the knowledge graph comprises:
   analyzing the knowledge graph to determine, for a first cohort, a most effective therapy, based on at least a subset of the plurality of pair-wise comparisons; and
   determining that an efficacy of the most effective therapy is below a predefined threshold.

15. The computer program product of claim 10, wherein processing the plurality of documents to determine the plurality of pair-wise comparisons comprises, for at least a first document in the plurality of documents:
   identifying and extracting, based on identifying comparative language, a conclusion specified within natural language text of the first document, wherein the conclusion comprises a comparison between two or more therapies of the plurality of therapies;
   determining a sentiment of the extracted conclusion, with respect to at least one therapy of the plurality of therapies; and
   identifying one or more cohorts of patients that are associated with the first document.

16. A system comprising:
one or more computer processors; and
a memory containing a program which when executed by the one or more computer processors performs an operation, the operation comprising:
   receiving a plurality of documents, each comprising digitally encoded natural language text data;
   processing the plurality of documents to determine a plurality of pair-wise comparisons between a plurality of therapies, wherein each of the plurality of pair-wise comparisons indicates a relative efficacy of at least one therapy in the plurality of therapies, as compared to at least one other therapy in the plurality of therapies;
   generating a knowledge graph, by operation of one or more processors, comprising aggregating the plurality of pair-wise comparisons, wherein the knowledge graph comprises a multidimensional representation of relative efficacies of the plurality of therapies with respect to a plurality of cohorts and a plurality of outcomes;
   updating the knowledge graph when new published literature becomes available;
   analyzing the knowledge graph to identify one or more knowledge gaps within the knowledge graph; and
   generating a score for a first knowledge gap of the one or more knowledge gaps, comprising:
      identifying a cohort associated with the first knowledge gap;
      determining a number of patients in the cohort; and
      identifying a most effective therapy for the cohort; and
   outputting an indication of the identified one or more knowledge gaps and the score for the first knowledge gap.

17. The system of claim 16, wherein analyzing the knowledge graph to identify one or more knowledge gaps within the knowledge graph comprises:
   determining that a first therapy and a second therapy have not been compared, in the plurality of documents, with respect to a first cohort; and
   determining that an efficacy of the first therapy and an efficacy of the second therapy are both above a predefined threshold efficacy.

18. The system of claim 16, wherein analyzing the knowledge graph to identify one or more knowledge gaps within the knowledge graph comprises:
   determining that an overall relative efficacy of a first therapy, as compared to a second therapy, is inconclusive based on at least one of:
      (i) determining that a number of documents, of the plurality of documents, that have compared the first and second therapies is below a predefined threshold; or
      (ii) determining that a first of the plurality of pair-wise comparisons contradicts a second of the plurality of pair-wise comparisons.

19. The system of claim 16, wherein analyzing the knowledge graph to identify one or more knowledge gaps within the knowledge graph comprises:
   identifying a first subset of the knowledge graph, wherein the first subset is connected by one or more pair-wise comparisons of the plurality of pair-wise comparisons;
   identifying a second subset of the knowledge graph, wherein the second subset is connected by one or more pair-wise comparisons of the plurality of pair-wise comparisons; and determining that the first and second subsets of the knowledge graph are disconnected from each other.

20. The system of claim 16, wherein analyzing the knowledge graph to identify one or more knowledge gaps within the knowledge graph comprises:

analyzing the knowledge graph to determine, for a first cohort, a most effective therapy, based on at least a subset of the plurality of pair-wise comparisons; and determining that an efficacy of the most effective therapy is below a predefined threshold.

* * * * *